US005272134A

United States Patent [19]

Berliner

[11] Patent Number: 5,272,134

[45] Date of Patent: Dec. 21, 1993

[54] FRAGRANCE COMPOSITIONS AND OTHER COMPOSITIONS WHICH CONTAIN HUMAN PHEROMONES

[75] Inventor: David L. Berliner, Atherton, Calif.

[73] Assignee: Erox Corporation, Menlo Park, Calif.

[21] Appl. No.: 907,940

[22] Filed: Jun. 24, 1992

Related U.S. Application Data

[63] Continuation-in-part of Ser. No. 856,435, Mar. 24, 1992.

[51] Int. Cl.[5] .................... A61K 7/46

[52] U.S. Cl. .................... 512/3; 512/15; 512/19

[58] Field of Search .................... 512/3, 15, 19

[56] References Cited

PUBLICATIONS

Berliner et al, J. Steroid Biochem. Molec. Biol., vol. 39, pp. 671-679 (1991).

Stansaas et al, J. Steroid Biochem. Molec. Biol., vol. 39, pp. 553-560 (1991).

Benjamin, Chem, Abst., vol. 96, #101,390q (1982).

Kirk-Smith et al, Chem. Abst., vol. 94, #115,047d (1981).

*Primary Examiner*—James H. Reamer

*Attorney, Agent, or Firm*—Morrison & Foerster

[57] ABSTRACT

The invention concerns novel, non-therapeutic fragrance compositions and other compositions containing an odorant and a naturally occurring human pheromone. The invention also concerns fragrance compositions containing mixtures of naturally occurring human pheromones. The human pheromones disclosed are steroids which desirably belong to two distinct chemical classes: 16-Androstenes and Estrenes.

26 Claims, 16 Drawing Sheets

I R = H
II R = $COOCH_3$

1

2

3

III R = H

IV R = $COOCH_3$

4

5 $R^1$ = OH; $R^2$ = H (48%)

6 $R^1$ = H; $R^2$ = OH (48%)

VII

8

7

11

14

12

15

13

16

17

18

19 20 21 22

VII 23

24 25

FRAGRANCE COMPOSITIONS AND OTHER COMPOSITIONS WHICH CONTAIN HUMAN PHEROMONES

CROSS-REFERENCE TO RELATED APPLICATIONS

This application is a continuation-in-part of the pending U.S. patent application entitled "Fragrance Compositions Containing Human Pheromones", filed 24 Mar. 1992, U.S. Ser. No. 07/856,435, which is hereby incorporated by reference.

This application may also relate to two copending U.S. patent application Ser. No. 07/708,936, filed 31 May 1991, and U.S. Ser. No. 07/707,862, filed 31 May 1991.

FIELD OF THE INVENTION

This invention is generally related to the fields of personal care products, cosmetics and fragrances and to compositions of matter used in consumer products. More specifically, the invention pertains to novel fragrance compositions and personal care products containing such fragrance compositions. This invention also pertains to the class of pheromones which are active in humans, and to the incorporation of pheromones into various compositions.

BACKGROUND ART

The present invention relates to cosmetics, particularly fragrances, and to compositions of matter which contain human pheromones and which are useful in the manufacture of consumer products. Pheromones are biochemicals produced by an animal or individual which elicits a specific physiological or behavioral response in another member of the same species. Different pheromones are produced by the members of each sex and received by specialized receptors in the nasal passage of members of the opposite sex. The human pheromones referred to in this invention are certain 16-Androstene and/or Estrene steroids, some of which occur naturally in humans.

The steroid class of Androstenes are typified by testosterone, and are characterized by a 4-ring steroid structure with methylations at the 13- position and usually at the 10- position. 16-Androstenes are further characterized by a double bond at the 16- position. Some members of this group have been reported to act as pheromones in some mammalian species—for instance, 5α-Androst-16-en-3α-ol and 5α-Androst-16-en-3-one in pigs (Melrose, D. R., et al., *Br. vet. J.* (1971) 127:497–502). These 16-Androstenes, produced by the boar, induce mating behavior in estrus sows (Claus, et al., *Experimentia* (1979) 35:1674–1675).

Some studies have noted that, in some species, various characteristics of certain 16-Androstenes (including 5α-Androst-16-en-3α-ol and 5α-Androst-16-en-3-one), such as blood concentration, metabolism, and localization, are sexually dimorphic (Brooksbank, et al., *J. Endocr.* (1972) 52: 239–251; Claus, et al., *J. Endocr.* (1976) 68:483–484; Kwan, et al., *Med. Sci. Res.* (1987) 15:1443–1444). For instance, 5α-Androst-16-en-3α-ol and 5α-Androst-16-en-3-one, as well as 4,16-Androstadien-3-one, have been found at different concentrations in the peripheral blood, saliva and axillary secretions of men and of women (Kwan, T. K., et al., *Med. Sci. Res.* (1987) 15:1443–1444).

The possible function of some 16-Androstenes as human pheromones, to the extent of effecting choice and judgment, has been suggested (Id.; see also Gower, et al., "The Significance of Odorous Steroids in Axillary Odour", in, *Perfumery*, pgs 68–72, Van Toller and Dodd, Eds., Chapman and Hall, 1988); Kirk-Smith, D. A., et al., *Res. Comm. Psychol. Psychiat. Behav.* (1978) 3:379). Androstenol (5α-Androst-16-en-3α-ol) has been claimed to exhibit a pheromone-like activity in a commercial men's cologne and women's perfume (Andron™ for Men and Andron™ for Women by Jövan). Japanese Kokai No. 2295916, refers to perfume compositions containing Androstenol and/or its analogue. 5,16-Androstadien-3β-ol (and perhaps the 3α-ol) has also been identified in human axillary secretion (Gower, et al., Supra at 57–60.

Estrene steroids are typified by 17β-Estradiol (1,3,5(10)-Estratrien-3,17β-diol), and are characterized by a phenolic 1,3,5(10) A-ring and a hydroxy or hydroxy derivative, such as an ether or ester, at the 3-position. The pheromone properties of some Estrene steroids for some mammalian species has been described. Michael, R. P. et al., *Nature* (1968) 218:746 refers to Estrogens (particularly Estradiol) as a pheromonal attractant of male rhesus monkeys. Parrot, R. F., *Hormones and Behavior* (1976) 7:207–215, reports Estradiol benzoate injection induces mating behavior in ovariectomized rats; and the role of the blood level of Estradiol in male sexual response (Phoenix, C. H., *Physiol. and Behavior* (1976) 16:305–310) and female sexual response (Phoenix, C. H., *Hormones and Behavior* (1977) 8:356–362) in Rhesus monkeys has been described.

The human pheromones described in this application have been referred to previously in applicant's U.S. Ser. No. 07/707,862, filed May 31, 1991, U.S. Ser. No. 07/708,936, filed May 5, 1991, P.C.T. application No. PCT/US92/00219, filed Jan. 7, 1991, and P.C.T. application No. PCT/US92/00220, filed Jan. 7, 1991, all of which are pending.

The most likely means of communication of a putative human pheromone is the inhalation of a naturally occurring pheromone present on the skin of another. Several 16-Androstene steroids, including 5α-Androst-16-en-3α-ol and 5α-Androst-16-en-3-one, 4,16-Androstadien-3-one, 5,16-Androstadien-3β-ol, and perhaps 5α-Androstadien-3α-ol, are naturally occurring in humans and may be present on the skin. It is estimated that the naturally occurring maximum concentration of all 16-Androstene steroids on human skin is from 2 to 7 $ng/cm^2$. During intimate contact it is estimated that a human would be exposed to no more than 700 ng of a naturally occurring steroid. Since these compounds are relatively non-volatile, it is estimated that, even during intimate contact, a human subject would inhale no more than 0.7 pg of a naturally occurring steroid from the skin of another. The subject invention is effective because it delivers a much larger amount of the active pheromone steroids than does normal intimate contact between individuals.

There is however, little agreement in the literature as to whether or not any putative pheromone actually plays a role in the sexual or reproductive behavior of mammals, particularly of humans. See: Beauchamp, G. K., et al., "The Pheromone Concept in Mammalian Chemical Communication: A Critique", in: *Mammalian Olfaction, Reproductive Processes, and Behavior*, Doty, R.

L., Ed., Academic Press, 1976. See also, Gower, et al., supra at 68–73.

Receptors for pheromones are found in the vomeronasal organ (VNO), a small structure which opens to the nasal passage in normal individuals (Moran, D. T., et al., *J. Steroid Biochem. and Molec. Biol.* (1991) 39:545; Stensaas, L. J., et al., *J. Steroid Biochem. and Molec. Biol.* (1991) 39:553; Garcia-Velasco, et al., *J. Steroid Biochem. and Molec. Biol.* (1991) 39:561). An odor does not bind to a VNO receptor—only a pheromone. A pheromone-specific change in the electrical potential of VNO receptor epithelium can be measured as described by Monti-Bloch, L., et al. (*J. Steroid Biochem. and Molec. Biol.* (1991) 39:573). This receptor binding activity is an essential characteristic of an active pheromone.

The compositions of many commercial perfumes and fragrances contain mammalian pheromones. Since pheromones are generally species specific, the mammalian pheromones found in commercial perfumes do not function as a pheromone, but instead provide a fixative note in the overall composition of the fragrance. Thus the perfumes, personal care products and cosmetics now available do not bind to pheromone receptors in the VNO and do not stimulate the vomeronasal nerve which communicates with the hypothalamus of the brain. Furthermore, in some cases the use of animal pheromones, or synthetics related to animal pheromones, may cause skin irritations or allergic responses in some individuals. Still further, since the source of animal pheromones used in fragrances are the anal glands of the contributing animal some individuals find it objectionable to use these substances. Finally, since none of the major ingredients found in commercial fragrances occur naturally on the human skin, the resulting scents are not natural human scents.

It would be preferable for a fragrance to contain naturally occurring human pheromones since this would result in stimulation of both olfactory (scent) receptors and pheromone receptors, would reduce the likelihood of irritation or an allergic response, would provide a more attractive composition for personal application, and would have a more natural human scent.

Further, certain compositions of matter such as fibrous paper tissues, paints, wax candles, incense and the like can be improved by addition of human pheromones.

SUMMARY OF THE INVENTION

Accordingly, it is a primary object of the invention to address the above-mentioned needs in the art by providing fragrance compositions, and other compositions of matter, containing a naturally occurring human pheromone.

It is also an object of this invention to provide fragrance compositions, and other compositions of matter, which stimulate both olfactory receptors and pheromone receptors in the VNO.

It is another object of this invention to provide fragrance compositions, and other compositions of matter, which are unlikely to be irritating to the skin of individuals and are likely to be hypoallergenic when inhaled.

It is another object of this invention to provide fragrance compositions, and other compositions of matter, with the consumer appeal of a naturally occurring human pheromone.

It is another object of this invention to provide a fragrance composition, and other compositions of matter, with a natural human scent.

Additional objects, advantages and novel features of the invention will be set forth in part in the description which follows, and in part will become apparent to those skilled in the art upon examination of the following, or may be learned by practice of the invention.

Objects of this invention are achieved by providing a non-therapeutic, fragrance composition containing a perfumery odorant and a human pheromone. The pheromone generates an in vivo vomeronasal organ receptor binding potential in a human subject.

Objects of this invention are also achieved by providing a fragrance composition containing a perfumery odorant and a steroidal compound selected from the group consisting of Androsta-4,16-dien-3-one, Androsta-4,16-dien-3α-ol, Androsta-4,16-dien-3β-ol, 19-nor-4,16-Androstadien-3-one, 19-nor-10-OH-4,16-Androstadien-3one, 19-OH-4,16-Androstadien-3-one, 5α-5,16-Androstadien-3β-ol, 5α-5,16-Androstadien-3α-ol, 19-nor-16-Androsten-3-one, 19-nor-16-Androsten-3α-ol, 19-nor-16-Androsten-3β-ol, 1,3,5(10)-Estratrien-3,17β-diol, 1,3,5(10)-Estratrien-3,16α,17β-triol, 1,3,5(10)-Estratriene-3-ol-17-one, 1,3,5(10),16-Estratetraen-3-ol methyl ether, 1,3,5(10),16-Estratetraen-3-yl acetate, 1,3,5(10),16-Estratetraen-3-yl propionate, 1,3,5(10),16-Estratetraen-3-ol, and any combinations thereof.

DETAILED DESCRIPTION

Figure 1:
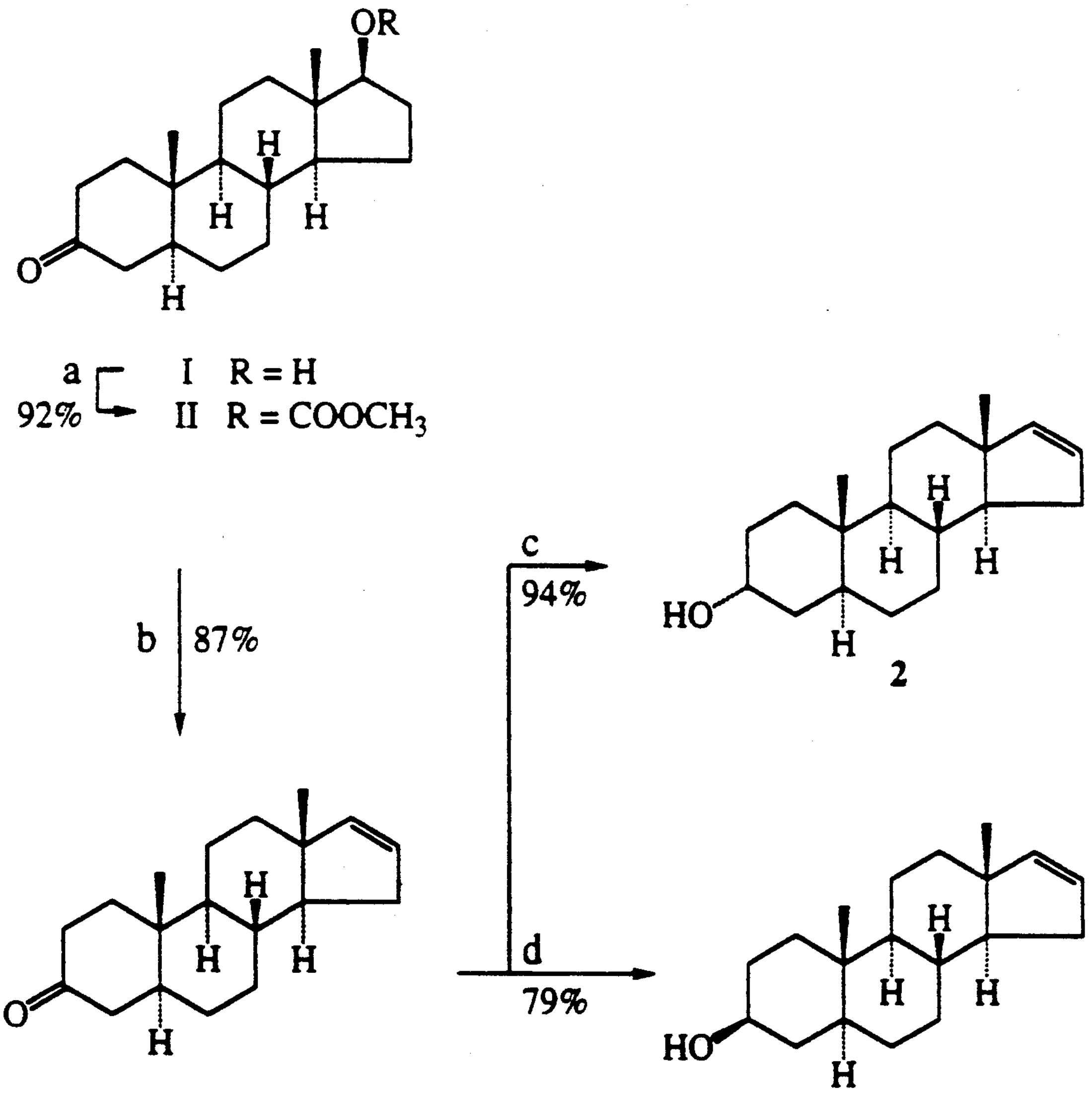
FIG. 1 schematically illustrates the synthesis of 5α-Androst-16-en-3-one, 5α-Androst-16-en-3α-ol and 5α-Androst-16-en-3β-ol.

Before the present compositions are disclosed and described, it is to be understood that this invention is not limited to specific fragrances, specific steroidal compounds, or the like, as such components may, of course, vary. It is also to be understood that the terminology used herein is for the purpose of describing particular embodiments only and is not intended as limiting.

It must be noted that, as used in the specification and the appended claims, the singular form "a", "an" and "the" include plural referents unless the context clearly dictates otherwise. Thus, for example, reference to "a perfumery odorant" includes mixtures of perfumery odorants, reference to "a human pheromone" includes mixtures of human pheromones, and the like.

A. Definitions

An "environmental fragrance" is a fragrance or odour which is used to odorize a volume of air rather than an individual or object. The source of the environmental fragrance may be an object, for example an object composed to gradually release a fragrance into the adjacent air.

An "odour" is any scent or smell, whether pleasant or offensive. An odour is consciously perceived by an individual when odorant molecules bind to the olfactory epithelium of the nasal passage. An "odorant" is an odorous substance. Perfumery materials, whether natural or synthetic, are described as odorants. A "perfumery odorant" is an odorant used for the principal purpose of providing a odor. A "scent" is the odour left behind by an animal or individual. People use perfumes to augment their natural scent.

A "perfume" or a "fragrance composition" is a specific pleasantly odorous cosmetic composition for topical application to an individual. Technically, perfumes are mixtures of a variety of substances, and may include natural materials of vegetable or animal origin, wholly or partly artificial compounds, or mixtures thereof. Dissolved in alcohol, these mixtures of various volatile fragrant substances release their scents into the air at normal temperatures. To a perfumer, only the extrait—the mixture which contains the highest proportion of fragrance concentrate and the least possible alcohol—is called perfume. Mixtures of lower concentration include eau de parfum, after shave, eau de toilette, eau de sport, splash cologne, eau de cologne, cologne, eau fraiche, and the like. In addition to the fragrance solutions which are diluted with alcohol, there are also those which are diluted with oil. Furthermore, compact and cream perfumes are produced by mixing up to 25% fragrance oil with solids such as paraffin or other waxes. Generally all the fragrance compositions described above are referred to as perfumes, and that is how the term is used herein.

A "pheromone" is a biochemical produced by an animal or individual which elicits a specific physiological or behavioral response in another member of the same species. In addition to physiological responses, pheromones can be identified by their species specific binding to receptors in the vomeronasal organ (VNO). Thus, human pheromones bind to human receptors. This can be demonstrated by measuring the change in the summated potential of neuroepithelial tissue in the presence of the pheromone. Human pheromones induce a change of at least about −5 millivolts in human neuroepithelial tissue of the appropriate sex (The binding of pheromones is generally sexually dimorphic). Naturally occurring human pheromones induce sexually dimorphic changes in receptor binding potential in vivo in the human VNO. Naturally occurring human pheromones can be extracted and purified from human skin and they can also be synthesized, as described herein. "Human pheromones" are pheromones which are naturally occurring in humans and effective as a specifically binding ligand in human VNO tissue, regardless of how the pheromone was obtained. Thus, both a synthesized and purified molecule may be considered a human pheromone.

"Sexually dimorphic" refers to a difference in the effect of, or response to, a compound or composition between males and females of the same species.

"Tissue paper" is a soft, fibrous, absorbent paper such as the type commonly used as a disposable hankerchief or as toilet paper. The "vomeronasal organ" is a cul-de-sac which opens to the nasal passage in humans and contains specialized receptor cells for pheromones.

B. Perfumes

The art and science of perfumery has been developed over several hundred years and is now well established. A brief summary of perfumery is provided herein. This subject is treated more fully in many publications including Wells, F. V. and M. Billot, *Perfumery Technology*, Ellis Horwood, Ltd., publisher, 2nd Ed. 1981.

1. Types of Ingredients

The diversity of the non-animal, natural products used in perfumery is considerable. In addition, advances in organic chemistry in the later nineteenth and the twentieth centuries have provided an equally broad diversity of artificial odorants as well as the ability to synthesize some of the naturally occurring components of natural odorants. Most perfumes combine preparations of naturally occurring materials with synthetic odorants.

The natural odorants that are generally employed in perfumery come from both animal and vegetable materials and can be assigned to the following six categories based on how they are treated:

1) Concrete oils—extracted with hydrocarbon solvents, without heat;
2) Absolute oils—alcohol extracted from concrete oils, without heat;
3) Essential oils—distilled from naturally occurring materials;
4) Expressed oils—physically removed directly from the natural material;
5) Isolates—fractionally distilled from essential oils;
6) Tinctures—obtained by prolonged alcohol extraction of naturally occurring materials.

A perfumer will typically have numerous oils, isolates, and tinctures from a variety of natural sources within each category. The perfumer will also have a vast array of artificial odorants and synthetics of naturally occurring compounds. Each of these materials is referred to as a "note". The art of perfumery involves the mixing of these various notes to produce a finished fragrance.

While there are many subjective approaches to the formulation of a perfume, most seem to incorporate the notion of top notes, middle notes and base notes. Top notes are very volatile and lack tenacity, or staying power. Middle notes are somewhat lower in volatility and are used as modifiers of the top notes. Bass notes are still lower in volatility and are long-lasting in odorous effect. Base notes are also referred to as fixatives of the fragrance. Notes of animal origin, or artificials which mimic animal notes, are usually base notes.

2. Animal Notes

Many commercial perfumes contain notes from animal sources, usually pheromones of the species from which the material is obtained, or synthetics and artificial notes which mimic the characteristics of animal notes. The principal animal-derived notes are the following:

1) musk—derived from the scent gland of the musk deer;
2) civet—obtained as a glandular secretion of the civet cat;
3) castoreum—obtained from the preputial follicle of the beaver; and
4) ambergris—a regurgitated or excreted material obtained from sperm whales.

The first three are pheromones for the species of origin, but since pheromones are species specific, they do not induce any pheromone-related behavior in humans. Animal notes are used as a fixative for the perfume fragrance. As a concentrate the odor of animal notes may not be pleasing, but when diluted, they contribute to the fragrance of the final product.

3. Human Pheromones

In the subject invention, naturally occurring human pheromones are used instead of, or in addition to animal pheromones, or their derivatives or homologues, as a component in compositions of matter. Naturally occurring human pheromones have several advantages.

The perfumed products previously available did not stimulate VNO receptors since an odorant which is not a pheromone for humans stimulates only the olfactory receptors of the nose. Fragrance compositions which are both pleasant smelling and also contain human pheromones will stimulate both olfactory receptors, and pheromone receptors in the VNO of individuals. Such a fragrance composition provides a broader olfactory stimulation than previously possible.

Perfumes are applied to the skin; however, the living skin, with its excretory and respiratory mechanisms, its secretions and variable temperature, is too changeable a medium to act as a good carrier of perfumes and frequently distorts the odour of the perfume in contact with it. Since human pheromones are normally present on human skin, a fragrance composition containing human pheromones would provide a more stable scent on the skin. Furthermore, the resulting scent would smell more naturally human. Some ingredients associated with commonly used animal notes (e.g. benzyl benzoate, paracresol, nitro-musks) have been found to cause skin irritation in some individuals. Furthermore, some individuals report an allergic response to some perfumes. Fragrance compositions containing naturally occurring human pheromones would be less likely than commonly used animal-related components to cause irritation or allergic response.

Finally, a perfume which uses naturally occurring human pheromones rather than material derived from the anal or preputial glands of animals would be inherently more appealing to many consumers.

As a concentrate, pheromones may or may not have a detectable odor. Since they bind to receptors which are physically and functionally distinct from olfactory receptors, they may or may not carry their own smell. However, some of the pheromones described herein do in fact have an odor. As a concentrate, the odor of these pheromones may not necessarily be pleasant. Thus, when diluted in a perfume the practical upper concentration limit is determined by the pleasantness of the resulting fragrance. Generally, human pheromones are present in the fragrance composition of the subject invention at a concentration of no more than about 200 μg/ml, more commonly no more than about 100 μg/ml, preferably no more than about 50 μg/ml, and more preferably no more than about 25 μg/ml.

Pheromones have a very low threshold of detectable receptor binding and they are effective at low concentrations. Generally, human pheromones are present in the fragrance composition of the subject invention at a concentration of at least about 50 ng/ml, more commonly at least about 100 ng/ml, preferably at least about 500 ng/ml, more preferably at least about 1 μg/ml.

C. Other Products Containing Pheromones

Perfumes are commonly used per se as a personal care product. However, odours can be used in a variety of personal care products, household products and industrial products. The use of human pheromones per se, or perfumes containing naturally occurring human pheromones in these other products falls within the scope of the subject application.

1. Personal Care Products

Fragrances containing human pheromones can be used in the preparation of cosmetics, make-up preparations, toilet and beauty preparations, bath and beauty soaps, bath oils, face and body creams and oils, underarm deodorants and the like. The preparations of these personal care products are known to those skilled in the art. These products frequently contain a fragrance. A human pheromone or a fragrance containing human pheromones is added to these products in the same way that fragrance per se may be added.

2. Environmental Odorants

Pheromones or fragrances containing human pheromones may also be used as environmental odorants as in air fresheners and the like. The fragrance and pheromone can be dispensed into the air by use of an aerosol dispenser, or by preparations of liquid, gel or solid compositions containing fragrance and pheromone which slowly release the pheromone, or fragrance and pheromone, into the air by exposure of the composition to the atmosphere.

For aerosol administration, the active ingredient is preferably supplied in a liquid or finely divided form along with a surfactant and a propellant. Typical percentages of active ingredients are 0.001 to 2% by weight, preferably 0.004 to 0.10%.

Surfactants must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, olestearic and oleic acids with an aliphatic polyhydric alcohol or its cyclic anhydride such as, for example, ethylene glycol, glycerol, erythritol, arabitol, mannitol, sorbitol, and hexitol anhydrides derived from sorbitol (the sorbitan esters sold under the trademark "Spans") and the polyoxyethylene and polyoxypropylene derivatives of these esters. Mixed esters, such as mixed or natural glycerides, may be employed. The preferred surface-active agents are the oleates or sorbitan, e.g., those sold under the trademarks "Arlacel C" (sorbitan sesquioleate), "Span 80" (sorbitan monoleate) and "Span 85" (sorbitan trioleate). The surfactant may constitute 0.1-20% by weight of the composition, preferably 0.25-5%.

The balance of the composition is ordinarily propellant. Liquefied propellants are typically gases at ambient conditions, and are condensed under pressure. Among suitable liquefied propellants are the lower alkanes containing up to five carbons, such as butane and propane; fluorinated or fluorochlorinated alkanes, such as are sold under the trademark "Freon". Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

An alternative means of releasing fragrance and pheromone into a designated air space is by means of gradual evaporation and release into the atmosphere from a liquid, semi-solid or solid composition containing a pheromone or a fragrance and pheromone. A human pheromone or a fragrance containing a human pheromone may be incorporated into the composition in a variety of ways depending on the nature of the composition.

If the composition is a liquid, gel, cream or ointment, and the pheromone ingredient is soluble in the composition it can simply be dissolved in the composition. If the pheromone ingredient is slightly soluble or insoluble in the composition, a suspension can be prepared by addition and mixing. In some cases such as room odorants, car odorants and the like, the composition containing pheromone is applied in a liquid state and remains liquid during evaporation. In other cases, such as paints and the like, the composition containing pheromone is applied as a liquid and then solidifies, leaving the pheromone to slowly evaporate from the solid.

If the composition is solid, the pheromone ingredient can be added by first melting the solid up to a maximum temperature of 100 degrees C., preferably 75 degrees C., more preferably 50 degrees C., adding the pheromone ingredient and then allowing the mixture to cool and solidify. This approach may be used with wax or resin for example. Alternatively, the pheromone ingredient may first be mixed in a volatile solvent such as ethanol, dimethyl sulfoxide or the like, and then mixed with an absorbent solid composition such as tissue paper, cloth and the like. The solvent then evaporates leaving the pheromone residue in the solid composition, from which the pheromone slowly evaporates into the atmosphere.

The uses of fragrance compositions containing human pheromones, as provided herein, are examples of alternative uses which fall within the intended scope of the claims and do not limit the intended scope of use of this invention.

3. Other Products

This mixture includes other products such as fibrous materials which will absorb pheromones with or without fragrances. For instance, cloth, papers (including tissue papers), clothing, paper towels, stationery and the like. These products need not contain a fragrance.

D. Human Pheromones

As described herein human pheromones generate a change in receptor potential in the VNO of human subjects. The naturally occurring human pheromones identified to date are steroids which fall into two classes—16-Androstenes and Estrenes. The biological activity of human pheromones is sexually dimorphic. 16-androstene pheromones generate a greater change in receptor potential of women than of men. Conversely, estrene pheromones generate a greater change in the receptor potential of men than of women.

16-Androstene steroids are aliphatic polycyclic hydrocarbons characterized by a four-ring steroidal structure with a methylation at the 13- position, and a double bond between the 16- and 17- positions. An Androstene steroid is commonly understood to mean that the compound has at least two methylations, at the 13- position and the 10- position, thereby creating 18- position and 19- position carbons respectively. Unless a compound is explicitly described as "19-nor" it is understood that the compound does have a 19- carbon group. However; it is intended that 19-nor-16-Androstenes are generally regarded as 16-Androstene steroids for the purpose of the present invention.

Estrene steroids are aliphatic polycyclic hydrocarbons with a four-ring steroidal structure, a aromatic 1,3,5(10) A-ring, a methylation at the 13-position and a hydroxyl at the 3-position.

In describing the location of groups and substituents of 16-Androstene and Estrene steroids, the following numbering system will be employed.

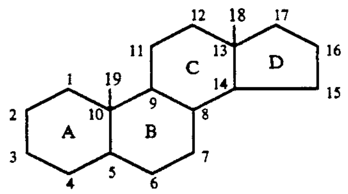

1. 16-Androstenes Useful in Conjunction with the Invention

The invention is directed to fragrance compositions containing a human pheromone which may be included in a group known as Androstene steroids of which testosterone (17-hydroxy-$\Delta^4$-androstene-3-one) is an example, and to combinations of Androstene and Estrene steroids. Specifically included are those steroids disclosed in the U.S. patent application Ser. No. 07/903,604 filed Jun. 24, 1992, the entirety of which is incorporated by notice. 16-Androstenes are further characterized by a double bond at position 16-.

The 16-Androstenes of this invention have the formula:

I

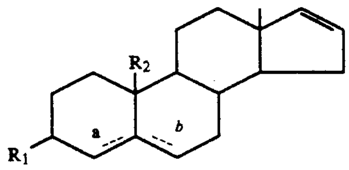

wherein $R^1$ is selected from the group consisting of oxo, α-(β-) hydroxy, α-(β-) acetoxy, α-(β-) propionoxy, α-(β-) methoxy, α-(β-) lower acyloxy, α-(β-) lower alkyloxy, and α-(β-) benzoyloxy; $R^2$ is selected from the group consisting of hydrogen, hydroxy, acyl, acyloxy, alkoxy, methyl, hydroxymethyl, acylmethyl, acyloxymethyl, alkoxymethyl, lower alkyl, hydroxyalkyl, acylalkyl, acyloxyalkyl, and alkoxylalkyl; and "a" and "b" are alternative sites for an optional double bond.

Preferred embodiments include $^{4,16}$Androstadien-3-one ($R^4$=oxo, a=double bond, $R^5$=methyl, commercially available from Steraloids, Inc., also referred to as Androstadienone), and 19-hydroxy-4,16-androstadien-3-one ($R^4$, a=double bond, $R_5$=hydroxymethyl), 4,16-Androstadien-3α(β)-ol ($R_4$=hydroxy, a=double bond, $R^5$=methyl), 19-nor-4,16-Androstadien-3-one ($R^4$=oxo, a=double bond, $R^5$=hydrogen), and 19-nor-10-OH-4,16Androstadien-3-one ($R^4$=oxo, a=double bond, $R^5$=hydroxy), syntheses of which are described herein).

2. Estrenes Useful in Conjunction with the Invention

The invention is additionally directed to fragrance compositions containing a human pheromone which may be included in a group of Estrene Steroids, or to combinations of Estrene and 16-Androstene steroids. Specifically included are those steroids disclosed in the U.S. patent application Ser. No. 07/903,604, filed Jun. 24, 1993, the entirety of which is incorporated by notice. These Estrenes are structurally similar to Estradiol (also referred to as 1,3,5(10)-Estratriene-3,17β-diol), but are distinguished from Estradiol by the double bond at the 16-position.

These Estrenes have the formula:

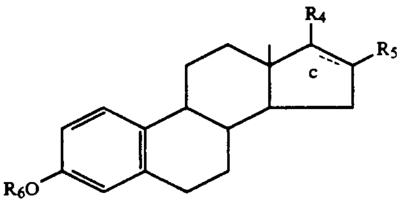

II wherein $R^4$ is selected from the group consisting of hydrogen, alkyl, oxo, α-hydroxy, β-hydroxy, sulfate, cypionate, acetate, and glucuronide; $R^4$ is selected from the group consisting of hydrogen, α-hydroxy, and β-hydroxy; $R^6$ is selected from the group consisting of hydrogen, lower alkyl, lower acyl, benzoyl, cypionyl, acetyl, glucuronide, propionyl, and sulfate; and "a" is an optional double bond.

These Estrenes can be distinguished from each other by variations at the 3-position, variations at the 17-position and variations at the 16-position, with an optional double bond at the 16-position. Preferred embodiments include 1,3,5(10)-Estratriene-3,17β-diol; 1,3,5(10)-Estratriene-3,16α,17β-triol; 1,3,5(10)-Estratrien-3-ol-17-one; and 1,3,5(10),16-Estratetraen-3-ol. These steroids are compounds known in the art and are commercially available e.g. from Sigma Chemical Co., Aldrich Chemical Co., etc. 1,3,5(10),16-Estratetraen-3-ol is available from Research Plus, Inc. and from Steraloids, Inc.

E. Synthesizing Human Pheromones

As indicated in Section D1, above, some of the preferred 16-Androstene pheromones are not commercially available. Their syntheses are provided herein.

1. Synthetic Methods a. Preparation of 3-Position, 5-Position, and 19-Nor Derivatives As shown in formula I, above, the compounds used in the methods of the present invention are 16-Androstene steroids substituted at the 3-, 5-, and 19- positions. Many of the 3- and 5- substituted steroids are known compounds which may be derived from 17-hydroxy-and 17-oxosteroids (commercially available e.g. from Aldrich Chemical Co) by elimination or reduction to the Δ16 homologue. The syntheses of most of these compounds are described by Ohloff (supra). As shown in FIG. 1, 17β-hydroxy-5α-androstan-3-one (I) and methyl chloroformate (a) in pyridine gives the methyl carbonate, 17β-methoxycarbonyloxy-5α-androstan-3-one (II) which provides a starting material for the 5α-androst-16-en-(3-one and 3-ols) (Ohloff, supra at pg 200).

Alkoxy derivatives are prepared from their corresponding hydroxy steroids by reaction with an alkylating agent such as trimethyloxonium fluoroborate, triethyloxonium fluoroborate or methylfluorosulfonate in an inert chlorocarbon solvent such as methylene chloride. Alternatively, alkylating agents such as alkyl halides, alkyl tosylates, alkyl mesylates and dialkylsulfate may be used with a base such as silver oxide or barium oxide in polar, aprotic solvents as for example, DMF, DMSO and hexamethylphosphoramide.

General procedures, for synthetic reactions of steroids are known to those skilled in art (See for example, Fieser, L. F. and M. Fieser, *Steroids*, Reinhold, N.Y. 1959). Where time and temperature of reactions must be determined, these can be determined by a routine methodology. After addition of the required reagents, the mixture is stirred under an inert atmosphere and aliquots are removed at hourly intervals. The aliquots are analyzed by means of thin-layer chromatography to check for the disappearance of starting material, at which point the work-up procedure is initiated. If the starting material is not consumed within twenty-four hours, the mixture is heated to reflux and hourly aliquots are analyzed, as before, until no starting material remains. In this case the mixture is allowed to cool before the work-up procedure is initiated.

Purification of the products is accomplished by means of chromatography and/or crystallization, as known to those skilled in the art.

1. Synthesis of 10-Hydroxy-Δ4,16-Androstadien-3-one

Figure 3:
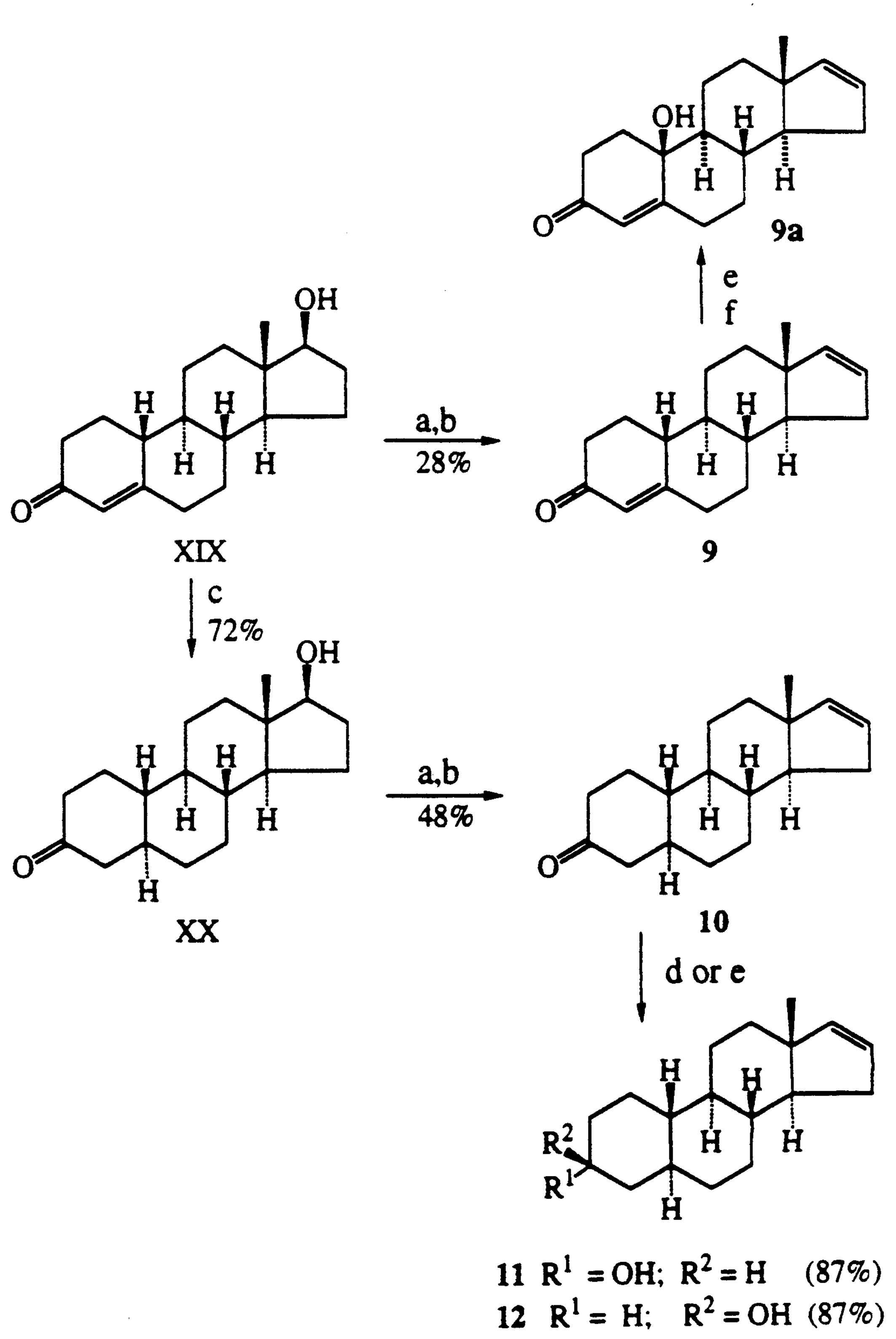
FIG. 3 schematically illustrates the synthesis of 19-nor-Δ4,16-Androstadien-3-one, 19-nor-Δ16-Androsten-3-one, 19-nor-Δ16-Androsten-3α-ol, 19-nor-Δ16-Androsten-3β-ol, and 19-nor-10-OH-Δ4,16-Androstadien-3-one.

As depicted in FIG. 3, 19-nor-$Δ^{4,16}$-androstadien-3-one in tetrahydrofuran is treated with one equivalent of lithium isopropylcyclohexylamide (LICA) (e), followed by molybdenum pentoxide in hexamethylphosphoramide/pyridine (MOOPH) (f). Aqueous work-up is followed by extraction and purification to yield 10-Hydroxy-Δ4,16-androstadien-3-one. The procedure follows that of Vedejs, *J. Org. Chem.* (1978) 43:188.

b. Preparation of 19-OH Derivatives

1. Synthesis of 19-OH-$Δ^{4,16}$-Androstadien-3-one

This compound has been disclosed as an intermediate in the synthesis of 19-oxo-3-aza-A-homo-5β-androstane (Habermehl, et al., *Z. Naturforsch.* (1970) 25b:191-195). A method of synthesizing this compound is provided. Additional methods of synthesis are provided in Examples 12 and 13.

EXAMPLES

The following examples are provided for illustrative purposes and should not be construed as limitations of the invention described in this application.

Abbreviations used in the examples are as follows aq.=aqueous; RT.=room temperature; PE=petroleum ether (b.p. 50°-70°); DMF=N,N-dimethylformamide; DMSO=dimethyl sulfoxide; THF=tetrahydrofuran.

EXAMPLE 1

5α-Androst-16-en-3-one (1)

This synthesis is depicted in FIG. 1. A solution of the methyl carbonate, 17β-methoxycarbonyloxy-5α-androstan-3-one (II) (9.6 g, 27.6 mmol) in toluene (200 ml) was pyrolyzed (b) in a Pyrex glass column (l=10 m, ϕ=9 mm) at 480° ($N_2$ stream ca. 11 ml/min) at a rate of ca. 1 g/h. The crude product (collected in two liquid $N_2$-cooled traps) was washed with sat. aq. $NaHCO_3$- and NaCl-solution, dried ($Na_2SO_4$) and evaporated. The residue (7.24 g, 97%) was recrystallized from PE at 0° to give 6.42 g (87%) of 1. An analytical sample was recrystallized from acetonitrile at RT. M.p. 142°-144°, $[a]_D=+35.6°$ (c=1.15) ([2]: m.p. 140°-141°, $[a]_D^{17}=+38°$ (c=2.08)). - IR. ($CDCl_3$): 1710s, 1595w. - $^1$H-NMR. (360 Mhz): 0.79 (s, 3 H); 1.05 (s, 3 H); 5.70 (m, 1 H); 5.84 (m, 1 H).

EXAMPLE 2

5α-Androst-16-en-3α-ol (2)

This synthesis is depicted in FIG. 1. To a 1M solution of lithium tris (1,2 dimethylpropyl) hydridoborate (c, commercially available from Aldrich, 2.5 ml, 2.5 mmol) at −55°, under $N_2$, was added a solution of ketone 1 (500 mg, 1.84 mmol) in THF (7 ml) and the mixture was allowed to warm up to RT. After 3 h, the mixture was cooled to −55° and hydrolyzed by addition of water (1 ml), followed by EtOH (3 ml). The boranes were oxidized by adding to the mixture at −55° 10% aq. NaOH-solution (5 ml), followed by 30% aq. $H_2O_2$-solution (3 ml), and stirring for 3 h at RT. Cyclohexane (100 ml) was added and the organic phase washed successively with water, sat. aq. $NaHSO_3$-solution and sat. aq. NaCl-solution; after drying ($Na_2SO_4$) and evaporation of the solvent, the residue was chromatographed on silica gel (60 g) with toluene/ethyl acetate 2:1. The axial alcohol 2 was eluted first (443 mg, 89%) and the second fraction contained the equatorial alcohol 3 (24 mg, 4.8%). An analytical sample of 2 was recrystallized from PE at 0°. M.p. 142°-144°, $[a]_D=+15°$ (C=1.33) ([2]: m.p. 143.5°-144°, $[a]_D^{16}=+13.9°$ (c=0.94)). - IR. ($CDCl_3$): 3625m, 3450w, 1590w. - $^1$H-NMR. (360 Mhz): 0.77 (s, 3 H); 0.82 (s, 3 H); 4.03 (m, $w_{½}\approx8$, 1 H); 5.70 (m, 1 H); 5.83 (m, 1 H).

EXAMPLE 3

5α-Androst-16-en-3α-ol (3)

This synthesis is depicted in FIG. 1. Ketone 1 (500 mg, 1.84 mmol) was reduced with sodium borohydride (d, 75 mg, 2 mmol) in THF/MeOH 5:1 (18 ml) at RT. (2 h). The crude product was chromatographed on silica gel (60 g) using toluene/ethyl acetate 2:1. After traces of the axial alcohol 2 (9 mg, 2%), the pure equatorial alcohol 3 (388 mg, 77%) was eluted. An analytical sample was recrystallized from MeOH/water. M.p. 124°-125°, $[a]_D=+14.2°$ (c=1.12) ([2]: m.p, 125°-127°, $[a]_D^{17}=+11.2°$ (c=0.76)). - IR. ($CDCl_3$): 3620m, 3430w, 1590w. - $^1$H-NMR. (360 Mhz): 0.77 (s, 3 H); 0.85 (s, 3 H); 3.60 t x t, J=11 and 5, 1 H); 5.70 (m, 1 H); 5.84 (m,1 H).

EXAMPLE 4

Androsta-4,16-dien-3-one (4)

Figure 2:
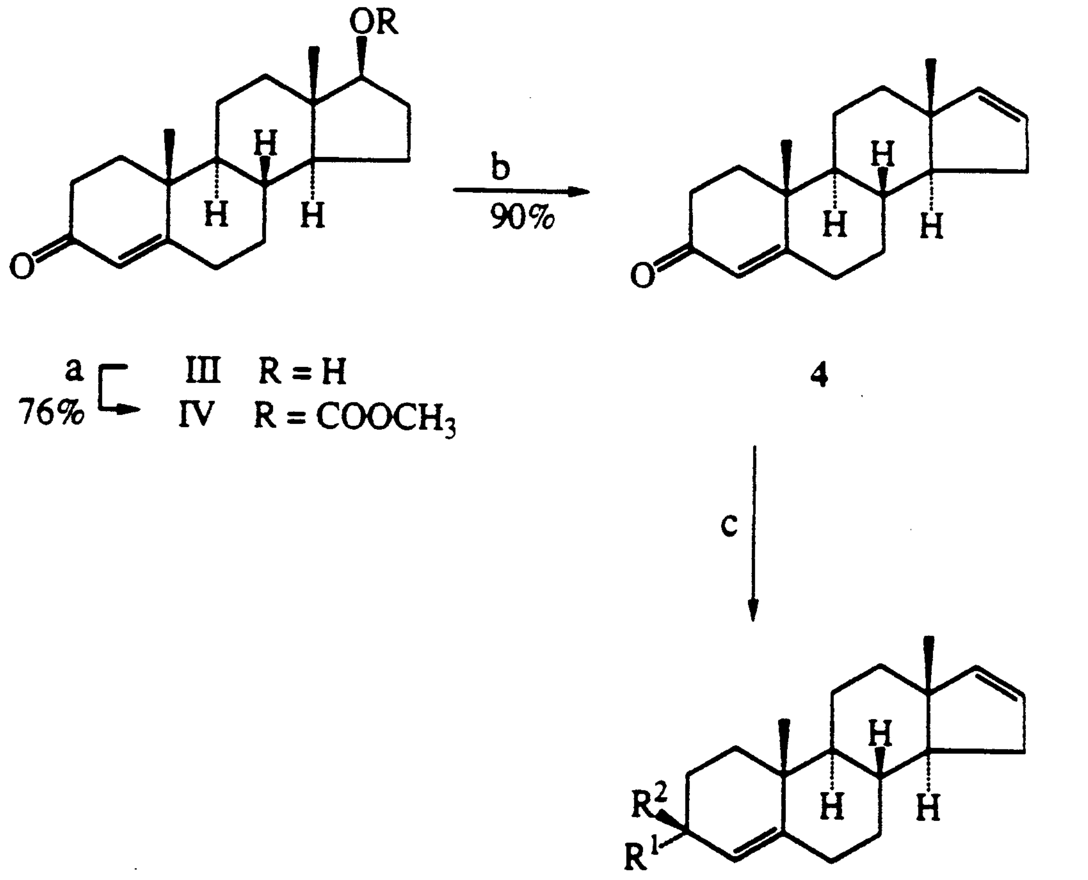
FIG. 2 schematically illustrates the synthesis of Androsta-Δ4,16-dien-3-one, Androstra-Δ4,16-dien-3α-ol, and Androsta-Δ4,16-dien-3β-ol.

This synthesis is depicted in FIG. 2. Several methods are known for the conversion of testosterone into Androsta-4,16-dien-3-one (Brooksbank et al., *Biochem. J.* (1950) 47:36). Alternatively, thermolysis (460°) of the methyl carbonate of testosterone gives Androsta-4,16-dien-3-one in 90% yield. 17β-Methoxycarbonyloxy-androst-4-en-3-one (IV) was prepared from testosterone (III. Fluka) with methyl chloroformate/pyridine (a) in 76% yield (after recrystallization from MeOH). M.p. 140°-141°, $[a]_D=+95.4°$ (C=1.10) - IR. ($CDCl_3$): 1740s, 1665s, 1450s, 1280s, $^1$H-NMR. (360 Mhz): 0.87 (s, 3 H); 1.20 (s, 3 H); 3.77 (s, 3 H); 4.53 (br. t, J=8, 1 H); 5.75 (s, 1 H). A solution of the methyl carbonate IV in toluene was pyrolyzed (b) as described for 1. Recrystallization of the crude product from acetone at RT. gave pure ketone 4 in 90% yield. M.p. 127°-129.5°, $[a]_D=+118.9°$ (c=1.32) ([3]: m.p. 131.5°-133.5° (hexane), $[a]_D^{16}+123°\pm3.5°$ (c=1.03)). - IR. ($CDCl_3$): 3050w, 1660s, 1615m. - $^1$H-NMR. (360 Mhz): 0.82 (s, 3 H); 1.22 (s, 3 H); 5.70 (m, 1 H); 5.73 (s, 1 H); 5.84 (m, 1 H).

EXAMPLE 5

Androsta-4,16-dien-3α-ol (5) and -3β-ol (6)

These syntheses are depicted in FIG. 2. Androsta-4,16-dien-3-one (4) was reduced at −55° with lithium tris(1,2-dimethylpropyl)hydridoborate in THF (c) as described for the preparation of 2 (FIG. 1). Chromatography on silica gel with $CH_2Cl_2$/ethyl acetate 9:1 gave pure axial alcohol 15 (48%, yield) and pure equatorial alcohol 6 (48% yield). Analytical samples were further purified by recrystallization (from PE at −30° for 5, from cyclohexane at RT. for 6).

Data of 5. M.p. 77°-79°, $[a]_D=+120.6°$ (c=1.26) - IR. ($CDCl_3$): 3620m, 3440m br., 1660m, 1595w. - $^1$H-NMR. (360 MHz): 0.79 (s, 3 H); 1.02 (s, 3 H); 4.07 (m, $w_{½}\approx10$, 1 H); 5.48 (d x d, J=5 and 2, 1 H); 5.71 (m, 1 H); 5.85 (m, 1 H).

Data of 6. M.p. 116°-119°, $[a]_D=+53.9°$ (c=1.28) ([47]: m.p. 116°-118°, $[a]_D=+59.3°$ (c=0.4) - IR. ($CDCl_3$): 3610m, 3420m br., 3050m, 1660m, 1590w. - $^1$H-NMR. (360 Mhz): 0.78 (s, 3 H); 1.08 (s, 3 H); 4.15 (m, $w_{½}\approx20$, 1 H); 5.30 (m, $w_{½}\approx5$, 1 H); 5.71 (m, 1 H); 5.85 (m, 1 H).

EXAMPLE 6

Androsta-Δ5,16-dien-3α-ol (7)

Figure 4:
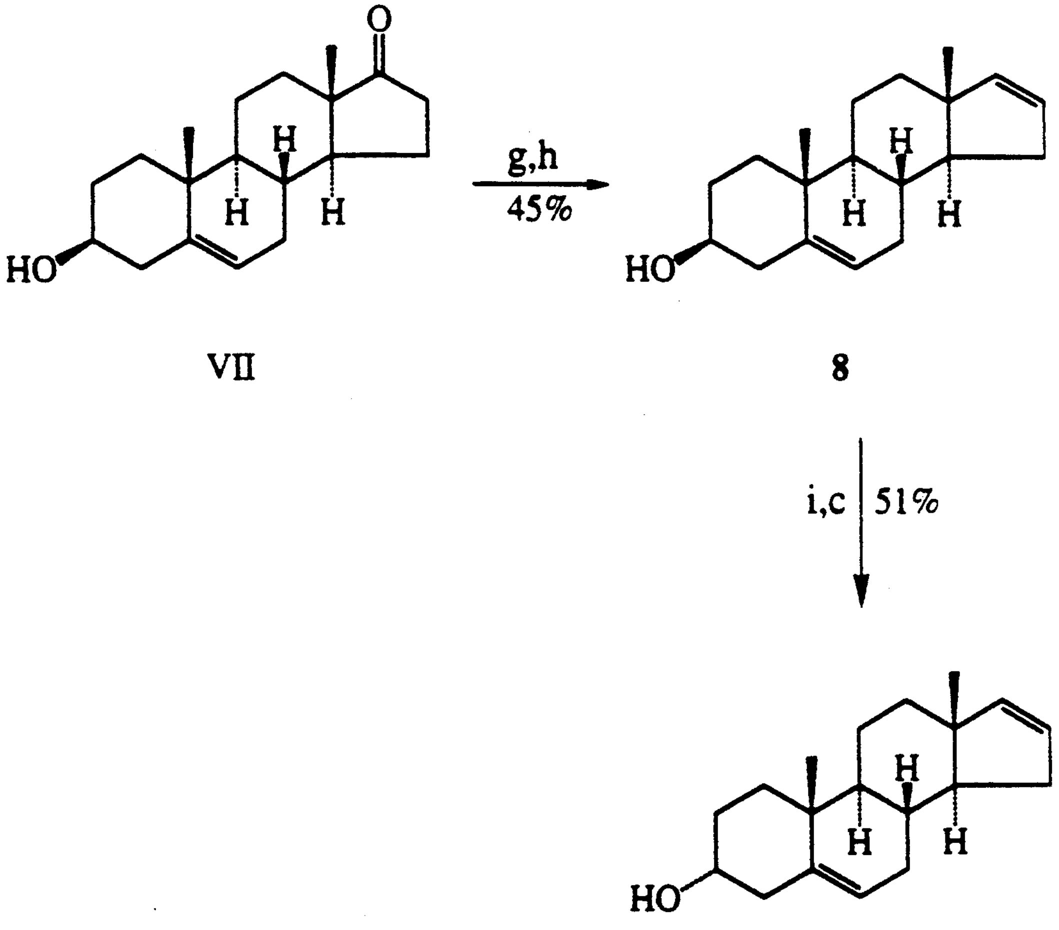
FIG. 4 schematically illustrates the synthesis of Androsta-Δ5,16-dien-3α-ol and Androsta-Δ5,16-dien-3β-ol.

This synthesis is depicted in FIG. 4. To a solution of alcohol 8 (545 mg, 2.0 mmol) in acetone (100 ml) at 0° under $N_2$ was added rapidly Jones reagent (i, 1.5 ml, ca. 4 mmol). After 5 min., the mixture was poured into a dilute phosphate buffer (Ph 7.2, 1200 ml) and extracted with ether. The extracts were washed with sat. aq. NaCl-solution, dried ($Na_2SO_4$) and evaporated to give mainly Androsta-5,16-dien-3-one as an oil (567 mg). The crude product was dissolved in THF (7 ml) and reduced with lithium tris (1,2-dimethylpropyl) hydridoborate (c) at −55° as described for the preparation of 2. The crude product (530 mg) was chromatographed on silica gel (100 g) with $CH_2Cl_2$/ethyl acetate 4:1 to give 280 mg (51%) of pure a-alcohol 7 (eluted first) and 13 mg of starting alcohol 8. A small sample of 7 was recrystallized from acetone/water at RT. - M.p.

138°, $[a]_D = -77.5°$ (c=1.2). - IR. ($CDCl_3$): 3580m, 3430m, 1665w, 1590w, - $^1$H-NMR. (360 Mhz): 0.80 (s, 3 H); 1.06 (s, 3 H); 4.02 (m, $w_{\frac{1}{2}} \approx 8$, 1 H); 5.44 (m, 1 H); 5.72 (m, 1 H); 5.86 (m, 1 H).

EXAMPLE 7

Δ5,16-Androstadien-3α-ol (8)

This compound was prepared in 73% yield by a known procedure (Marx, A. F., et al., Ger. Offen. 2,631,915; Chem. Abst. 87:23614p (1977)) from commercial (Fluka) 3α-hydroxy-androst-5-en-17-one (VII). M.p. 137°, $[a]_D = -71.9°$(c=1.5) ([48]: m.p. 140°-141°, $[a]_D - = 68°$. - IR. ($CDCl_3$): 3600m, 3420m br., 1670w, 1590w, - $^1$H-NMR. (360 MHz): 0.80 (s, 3 H); 1.05 (s, 3 H); 3.53 (m, $w_{\frac{1}{2}} \approx 22$, 1 H); 5.38 (m, 1 H); 5.72 (m, 1 H); 5.86 (m, 1 H). This synthesis is depicted in FIG. 4.

EXAMPLE 8

19-nor-Androsta-4,16-dien-3-one (9)

This synthesis is depicted in FIG. 3. 19-Nortestosterone (XIX) is commercially available, e.g. from Chemical Dynamics Corp. It provides the starting material for 19-Nor-16-androsten derivatives. 19-Nor-testosterone (XIX) (Chemical Dynamics Corp.) was converted into the known acetate (Hartman, J. A. et al., *J. Am. Chem. Soc.* (1956) 78:5662) with acetanhydride and pyridine (a). A solution of this acetate (4.8 g, 15.17 mmol) in toluene (10 ml) was pyrolyzed (b) at 540° (200 Torr, slow $N_2$-stream) in a glass tube packed with quartz pieces. Chromatography of the crude pyrolysate (3.1 g) on silica gel (150 g) with $CH_2Cl_2$ gave 1.1 g (28%) of the homogenous oily ketone 9; $[a]_D = +57.9°$ (c=1) ([27]: m.p. 71°-73°). - IR. ($CHCl_3$): 1660s, 1615m, 1585w, - $^1$H-NMR. (90 Mhz): 0.84 (s, 3 H); 5.82 (m, 2 H); 5.87 (br. s, 1 H).

EXAMPLE 9

19-nor-Δ16Androsten-3one (10))

This synthesis is depicted in FIG. 3. 19-Nortestosterone was reduced to 19-Nor-5α-androstan-17-ol-3-one (XX) with Lithium and ammonia (c) according to the method of Villotti, R., et al. (*J. Am. Chem. Soc.* (1960) 82:5693). Androsta-5α,17-diol-3-one (XX) was converted into the known acetate (Hartman, J. A. et al., *J. Am. Chem. Soc.* (1956) 78:5662) with acetanhydride and pyridine (a). A solution of 17β-acetoxy-5α-Estrane-3-one (8.0 g, 25.1 mmol) in octane/acetone 10:1 (22 ml) was pyrolyzed (b) at 550° (200 Torr, slow $Na_2$-stream). Chromatography of the crude product (5.4 g) on silica gel (600 g) with $CH_2Cl_2$ and recrystallization of the homogenous fractions from PE gave 3.13 g (48.3%) of the pure ketone 10. M.p. 51°-54°, $[a]_D = +72.8°$ (c=1.0). - IR. ($CHCl_3$): 1705s, 1585w, - $^1$H-NMR. (90 MHz): 0.79 (s, 3 H); 5.71 (m, 1 H); 5.87 (m, 1 H).

EXAMPLE 10

19-nor-Δ16-Androsten-3α-ol (II)

This synthesis is depicted in FIG. 3. L-Selectride (d, lithium tri(sec-butyl)hydridoborate, 4 ml of a 1M solution in THF, 4 mmol) was added dropwise at 0° to a solution of ketone 10 (800 mg, 3.10 mmol) in dry ether (5 ml). After stirring for 1 h at 0°, water was added (10 ml). The boranes were oxidized by adding 10% aq. NaOH-solution (5 ml), followed by 30% aq. $H_2O_2$-solution (3 ml) and stirring for 3 h at RT. After workup (ether), the crude product (790 mg, ca. 9:1 mixture of 11 and 12) was chromatographed on silica gel with $CH_2Cl_2$ to give 700° mg (87%) of pure alcohol 11. M.p. 119°-120°→123°-124° (from PE), $[a]_D = +40.6°$ (c=1.0). - IR. ($CHCl_3$): 3640m, 3500 br., 1585w. - $^1$H-NMR. (90 Mhz). 0.78 (s, 3 H); 4.09 (m, $w_{\frac{1}{2}} \approx 8$, 1 H); 5.71 (m, 1 H), 5.87 (m, 1 H).

EXAMPLE 11

19-nor-Δ16-Androsten-3α-ol (12)

This synthesis is depicted in FIG. 3. A solution of the ketone 10 (800 mg, 3.10 mmol) in dry ether (5 ml) was added dropwise at RT. to a slurry of $LiAlH_4$ (38 mg, 1 mmol) in ether (3 ml) (e). After 1 h, the mixture was hydrolyzed with 10% aq. $H_2SO_4$. After workup (ether), the crude product (802 mg, 9:1-mixture of 12 and 11) was chromatographed on silica gel with $CH_2Cl_2$. A small fraction of 11 (70 mg) was eluted first, followed by the main fraction of 12 (705 mg, 87%). M.p. 113°-115°, $[a]_D = +36.3°$ (c=1.0). - IR. ($CHCl_3$): 3640m, 3500 br., 1585w. - $^1$H-NMR. (90 MHz): 0.78 (s, 3 H); 3.60 (m, $w_{\frac{1}{2}} \approx 20$, 1 H); 5.71 (m, 1 H), 5.87 (m, 1 H).

EXAMPLE 12

Syntheses of 19-OH-Δ4,16-Androstadien-3-one (18)

Figures 1, 5:
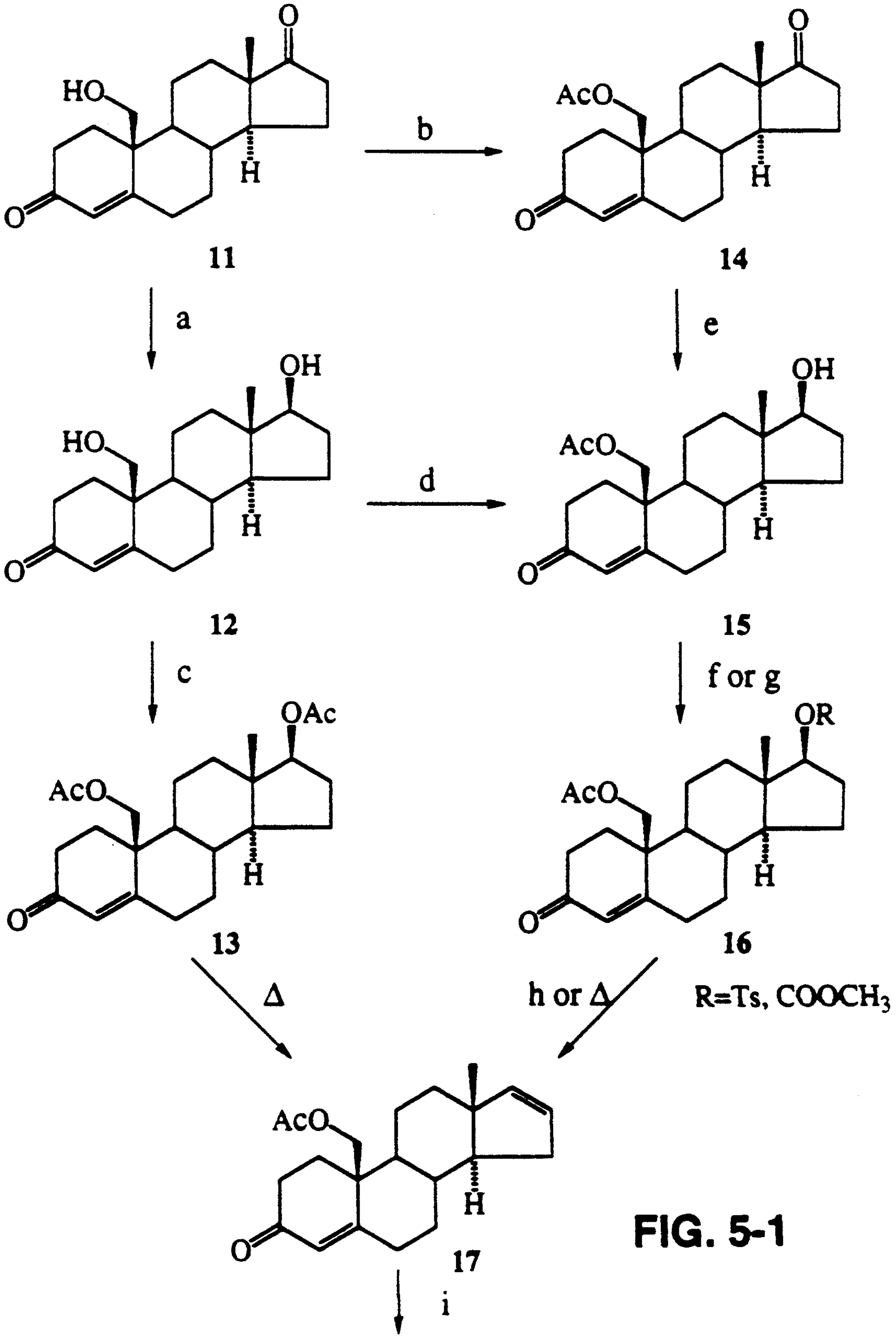
FIG. 5 schematically illustrates syntheses of 19-OH-Androst-Δ4,16-dien-3-one.
Figures 2, 5:
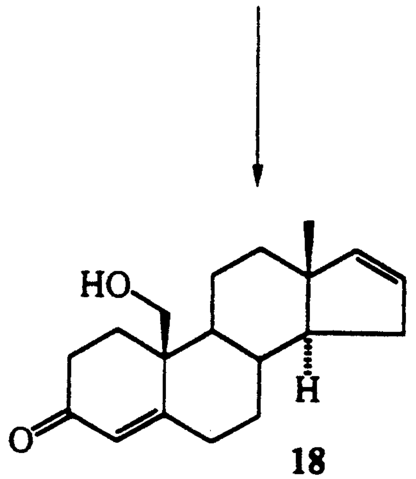

The following three methods of synthesis of 19-OH-$\Delta^{4,16}$-androstadien-3-one are depicted in FIG. 5.

Androst-4-en-17,19-diol-3-one (12):

Also known as 19-Hydroxytestosterone, this compound is commercially available from Steraloids, Inc. Alternatively, 19-hydroxyandrost-4-en-3,17-dione (11) is treated with potassium borohydride ($KBH_4$, a) in ethanol at −10° to 0° C. Aqueous work up is followed by extraction and purification to yield 19-hydroxytestosterone (12).

19-Acetoxyandrost-4-en-3,17-dione (14):

Androst-4-en-19-ol-3,17-dione (11) is treated with acetic anhydride ($Ac_2O$, b) in pyridine. Aqueous work-up is followed by extraction and purification to yield the acetate (14).

19-Acetoxytestosterone acetate (13):

19-Hydroxytestosterone (12) is treated with $Ac_2O$ in pyridine (c) with 4,4-dimethylaminopyridine catalyst. Aqueous work-up is followed by extraction and purification to yield the acetate (13).

19-Acetoxytestosterone (15) (method 1):

19-Hydroxytestosterone (12) is treated with $Ac_2O$ in pyridine (d). Aqueous work-up is followed by extraction and purification to yield the acetate (15).

19-Acetoxytestosterone (15) (method 2):

19-Acetoxyandrost-4-ene-3,17-dione (14) is treated with $KBH_4$ (e) in ethanol at −10° to 0° C. Aqueous work-up is followed by extraction and purification to yield the acetate (15).

19-Acetoxytestosterone tosylate (16,R=Ts):

19-Acetoxytestosterone (15) is treated with p-Toluenesulfonyl chloride (TsCl, f) in pyridine. Aqueous work-up is followed by extraction and purification to yield the tosylate (16,R=Ts).

19-Acetoxytestosterone methyl carbonate (16,R=$COOCH_3$):

19-Acetoxytestosterone (15) is treated with methyl chloroformate ($ClCOOCH_3$, g) in pyridine. Aqueous work-up is followed by extraction and purification to yield the methyl carbonate (16,R=$COOCH_3$).

19-Acetoxyandrosta-4,16-dien-3-one (17) (method 1):

19-Acetoxytestosterone acetate (13) is subjected to pyrolysis. The crude pyrolysate is purified to give the acetate (17).

19-Acetoxyandrosta-4,16-dien-3-one (17) (method 2):

19-Acetoxyandrone tosylate (16,R=Ts) is heated in 2,4,6-collidine (h). After cooling, aqueous work-up is followed by extraction and purification to yield the acetate (17).

19-Acetoxyandrosta-4,16-dien-3-one (17) (method 3):

19-Acetoxytestosterone methyl carbonate (16,R=$COOCH_3$) is subjected to pyrolysis. The crude pyrolysate is purified to give the acetate (17).

19-Hydroxyandrosta-4,16-dien-3-one (18):

19-Acetoxyandrosta-4,16-dien-3-one (17) is treated with potassium hydroxide in methanol (i). Aqueous work-up is followed by extraction and purification to yield the alcohol (18).

EXAMPLE 13

Alternate synthesis of 19-OH-$\Delta^{4,16}$-Androstadien-3-one (22)

Figure 6:
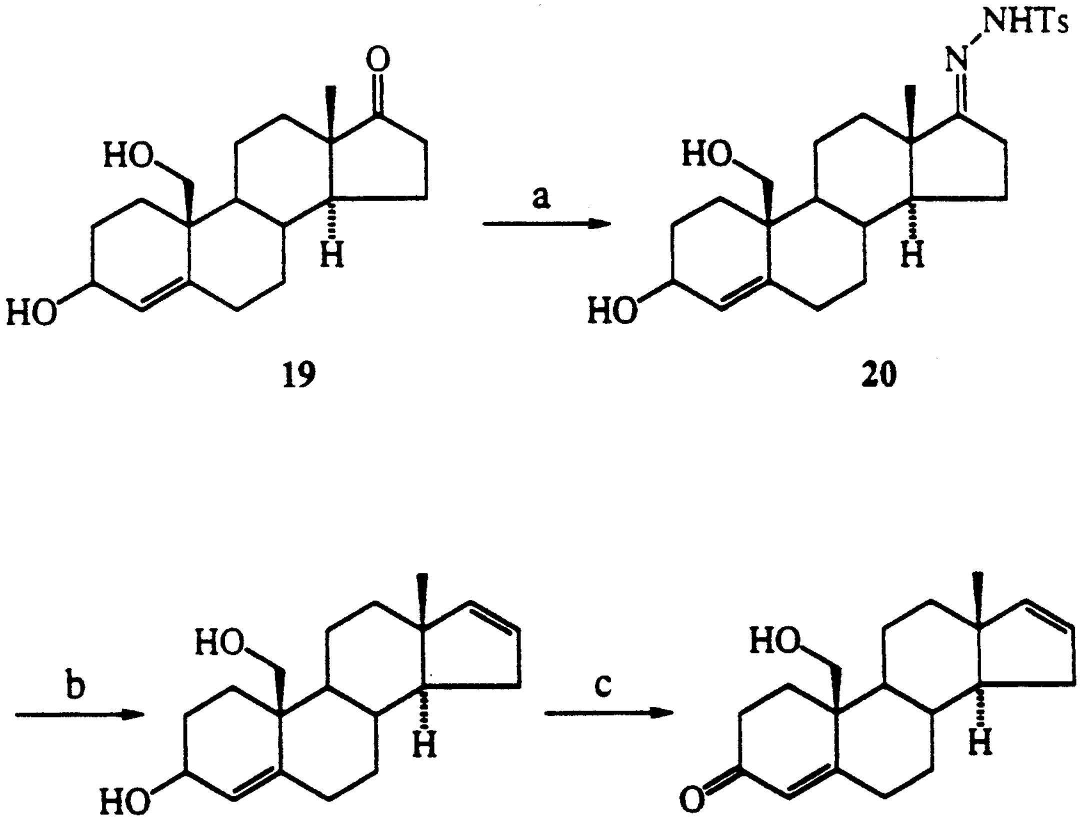
FIG. 6 schematically illustrates an alternate synthesis of 19-OH-Androsta-Δ4,16-dien-3-one.

The following method of synthesis is depicted in FIG. 6:

3,19-Dihydroxyandrost-4-en-17-one tosylhydrazone (20)

3,19-Dihydroxyandrost-4-en-17-one (19) is heated under reflux in methanol with one equivalent of p-toluenesulfonylhydrazide ($TsNHNH_{2,a}$) for 16 hours. After cooling, the mixture is evaporated to give the crude product. Purification yields the tosylhydrazone (20).

3,19-Dihydroxyandrosta-4,16-diene (21)

The tosylhydrazone (20) in tetrahydrofuran is treated with n-butyl lithium (BuLi, b) in hexane and the mixture is stirred at room temperature for 16 hours. Aqueous work up is followed by extraction and purification to yield the diene (21) .

19-Hydroxyandrosta-4,16-dien-3-one (22)

3,19-Dihydroxyandrosta-4,16-diene (21) is treated with manganese dioxide ($MnO_2$, c) in hexane. The mixture is filtered and evaporated to give the crude product. Purification yields the enone (22).

EXAMPLE 14

Alternate synthesis of Androsta-4,16-dien-3-one (25)

Figure 8:
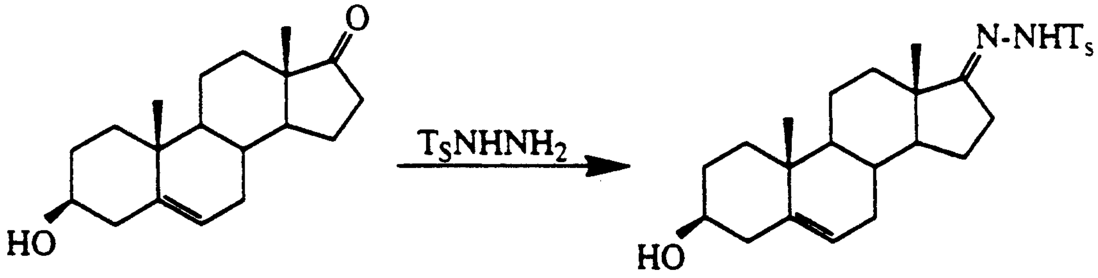
FIG. 8 schematically illustrates an alternate synthesis of Androsta-4,16-dien-3-one.
Figure 8:
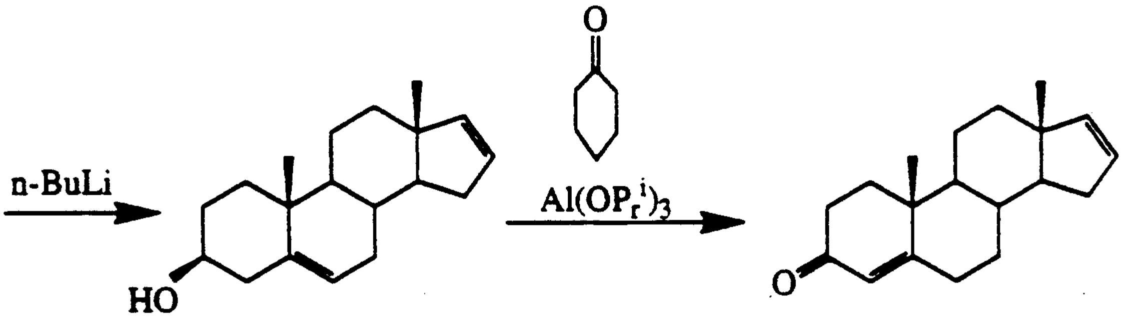

The following method of synthesis is depicted in FIG. 8:

Dehydroepiandrosterone p-Toluenesulfonylhydrazone (23)

Dehydroepiandrosterone (VII) (14.4 g, 50.0 m mole) and p-toluenesulfonylhydrazide (12.75 g, 68.5 m mole) in dry methanol (300 ml) were heated under reflux for 20 hours. The mixture was transferred to a conical flask and allowed to cool. The crystalline product was filtered off under suction and washed with methanol (50 ml). Further crops of product were obtained by sequentially evaporating the filtrate to 75 ml and 20 ml, and allowing to crystallize each time. Total yield was 21.6 g (95%).

Androsta-5,16-dien-3α-ol (24)

Dehydroepiandrosterone p-toluenesulfonylhydrazone (23) (22.8 g, 50.0 m mole) in dry tetrahydrofuran (1.0 liters) was cooled in a dry ice/isopropanol bath. The mixture was stirred while n-butyl lithium (125 ml of 1.6M solution in hexane, 200 m mole) was added. The mixture was allowed to warm to room temperature and was stirred for 24 hours. Water (50 ml) was added with cooling in ice. The mixture was poured into saturated ammonium chloride solution/ice (500 ml) and extracted with ether (x2). The organic layers were washed with saturated sodium bicarbonate solution (500 ml) and saturated sodium chloride solution (500 ml), dried ($MgSO_4$) and evaporated in vacuo to give the crude product. This was purified by flash chromatography on 190 g silica gel 60, 230–400 mesh, eluting with ethyl acetate/hexane (20:80→50:50) to give crystalline material. The product was recrystallized from methanol (45 ml)/3% hydrogen peroxide (8 ml) washing with methanol (30 ml)/water (8 ml) to give pure product (6.75 g, 50%).

Androsta-4,16-dien-3-one (25)

A solution of 10 g of Androsta-5,16-dien-3α-ol (24) in 475 cc of toluene and 75 cc of cyclohexanone was distilled (ca. 50 cc of distillate was collected) to eliminate moisture, 5 g of $Al(OPr^i)_3$ in 50 cc of toluene was added and the solution was refluxed for 1 hour. Water then was added, volatile components were removed by steam distillation and the residue was extracted with chloroform. Evaporation of the dried extract, followed by crystallization of the residue from chloroform-hexane, yielded 7.53 g of Androsta-4,16-dien-3-one (25). Another 0.97 g (total, 8.5 g, 86%) was obtained by chromatography of the mother liquor on neutral alumina.

EXAMPLE 15

Synthesis of Estra-1,3,5(10),16-tetraen-3-ol (28)

Figure 7:
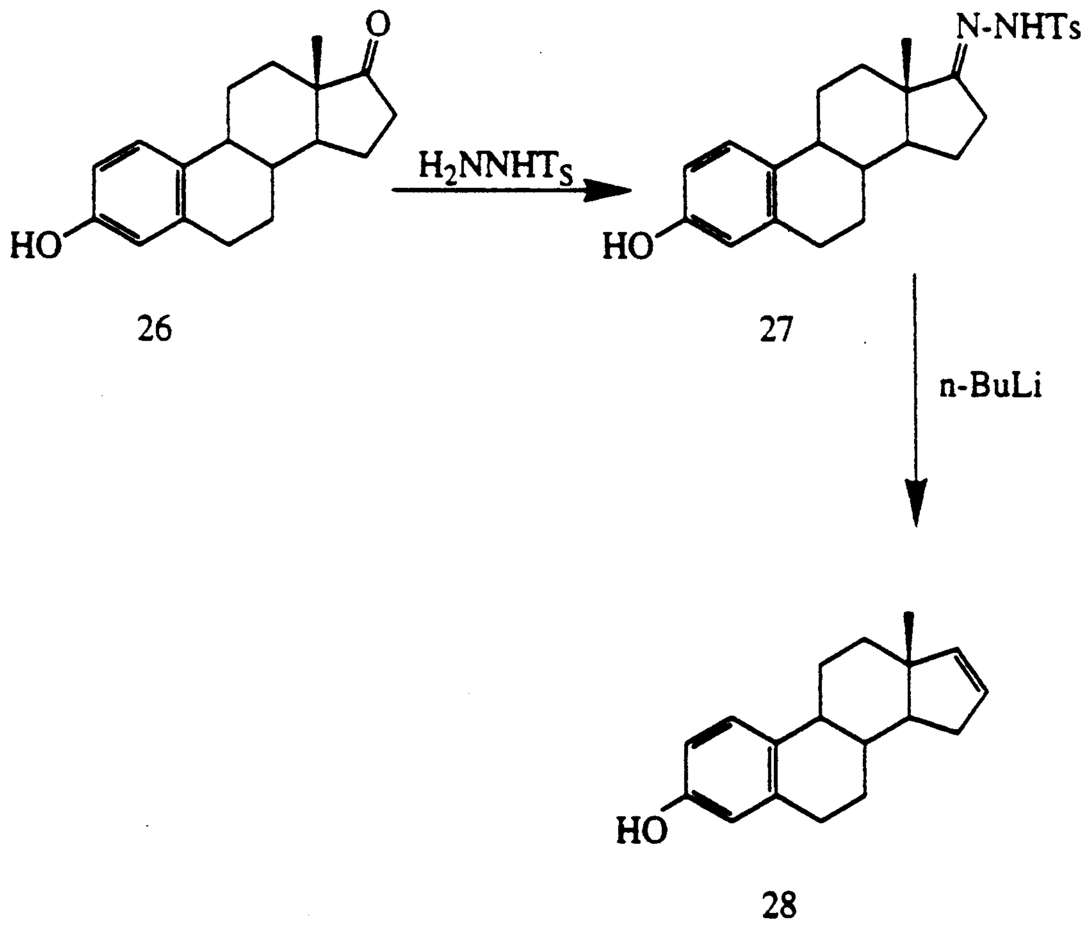
FIG. 7 schematically illustrates synthesis of 1,3,5(10),16-Estratetraen-3-ol.

The following method of synthesis is depicted in FIG. 7:

Estrone p-Toluenesulfonylhydrazone (27)

Estrone (26) (270 g, 1.00 mole) and p-toluenesulfonylhydrazide (232.8 g, 1.25 mole) in dry methanol (2.5 liters) were heated under reflux for 20 hours. The mixture was transferred to a conical flask and allowed to cool. The crystalline product was filtered off under suction and washed with methanol (300 ml). Further crops of product were obtained by sequentially evaporating the filtrate to 2000 ml, 800 ml and 400 ml, and allowing to crystallize each time. Total yield was 433.5 g (99%).

1,3,5(10),16-Estratetraen 3-ol (28):

Estrone p-toluenesulfonylhydrazone (27) (219.0 g, 500 m mole) in dry tetrahydrofuran (8.0 liters) was cooled in a sodium chloride/ice bath. The mixture was mechanically stirred while n-butyl lithium (800 ml of a 2.5M solution in hexane, 2.00 mole) was added via double-ended needle. The mixture was stirred at room temperature for 3 days. Ice (250 g) was added, followed by saturated ammonium chloride solution (500 ml). The phases were mixed by stirring and then allowed to settle. The aqueous phase was removed via aspiration with teflon tube and extracted with ether (500 ml). The two organic phases were sequentially washed with the same batch of saturated sodium bicarbonate solution (500 ml) followed by saturated sodium chloride solution (500 ml). The organic layers were dried ($MgSO_4$) and evaporated in vacuo to give crude product. This was subjected to flash filtration on 500 g silica gel 60, 230–400 mesh, eluting with ethyl acetate/hexane (25:75, 2.5 liters). The filtrate was evaporated in vacuo to give crystalline material. The product was recrystallized from methanol (300 ml)/water (75 ml) washing with methanol (80 ml)/ water (20 ml). Further recrystallization from ethyl acetate/hexane (12.5:87.5) gave pure product (88.9 g, 70%).

EXAMPLE 16

Electrophysiology of 16-Androstene Stimulation of the Human VNO and Olfactory Epithelium A non-invasive method has been employed to record local electrical potentials from the human vomeronasal organ (VNO) and from the olfactory epithelium (OE). Localized gaseous stimulation was applied to both nasal structures at different instances using specially designed catheter/electrodes connected to a multichannel drug delivery system. The local response of the VNO and the OE showed a correlation with the concentration of the stimulus.

The study was performed on ten clinically normal (screened) volunteers—2 males and 8 females, ranging in age from 18 to 85 years. The studies were conducted without general or local anesthetics.

The catheter/electrodes were designed to deliver a localized stimulus and simultaneously record the response. In the case of VNO recording, the right nasal fosa of the subject was explored using a nasoscope (nasal specula) and the vomeronasal opening was localized close to the intersection of the anterior edge of the vomer and the nasal floor. The catheter/electrode was gently driven through the VNO-opening and the electrode tip placed in the organ's lumen at 1 to 3 mm from the opening. The nasoscope was then removed. In the case of the OE, recording the procedure was similar except the positioning of the catheter/electrode was gently placed deep in the lateral part of the medial nasal duct, reaching the olfactory mucosa.

Localized gaseous stimulation was done through the catheter/electrode. A constant stream of clean, nonodorous, humidified air at room temperature was continuously passed through a channel of the stimulating system. The stimulating substances were diluted in propylene glycol, mixed with the humidified air, and puffed for from 1 to 2 seconds through the catheter-/electrode. It is estimated that this administration provides about 25 ρg of steroid to the nasal cavity.

Figure 9A:
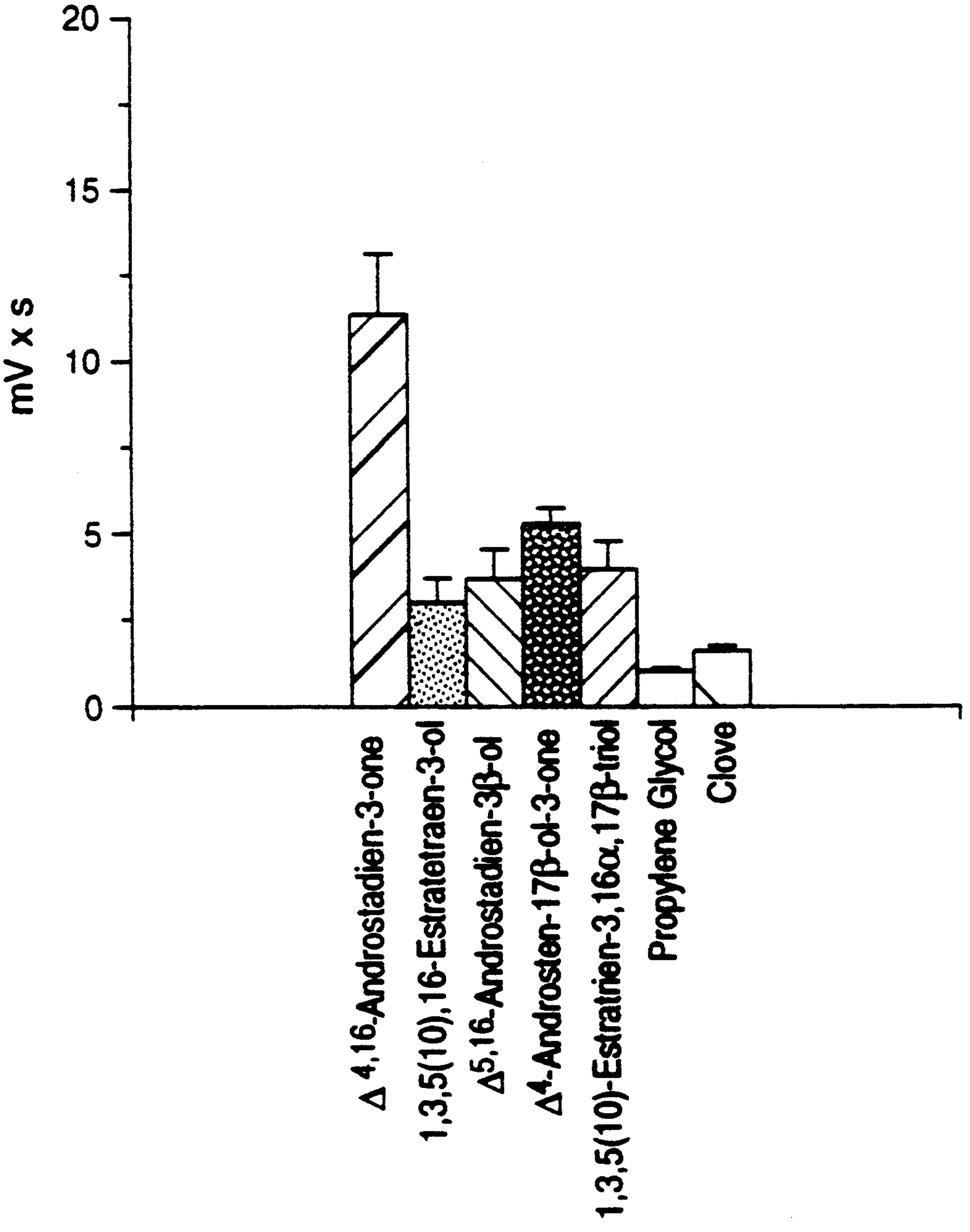
FIG. 9 is a graphic representation of the electrophysiological effect of the localized administration of particular 16-Androstene steroids to the vomeronasal organ and to the olfactory epithelium.
Figure 9B:
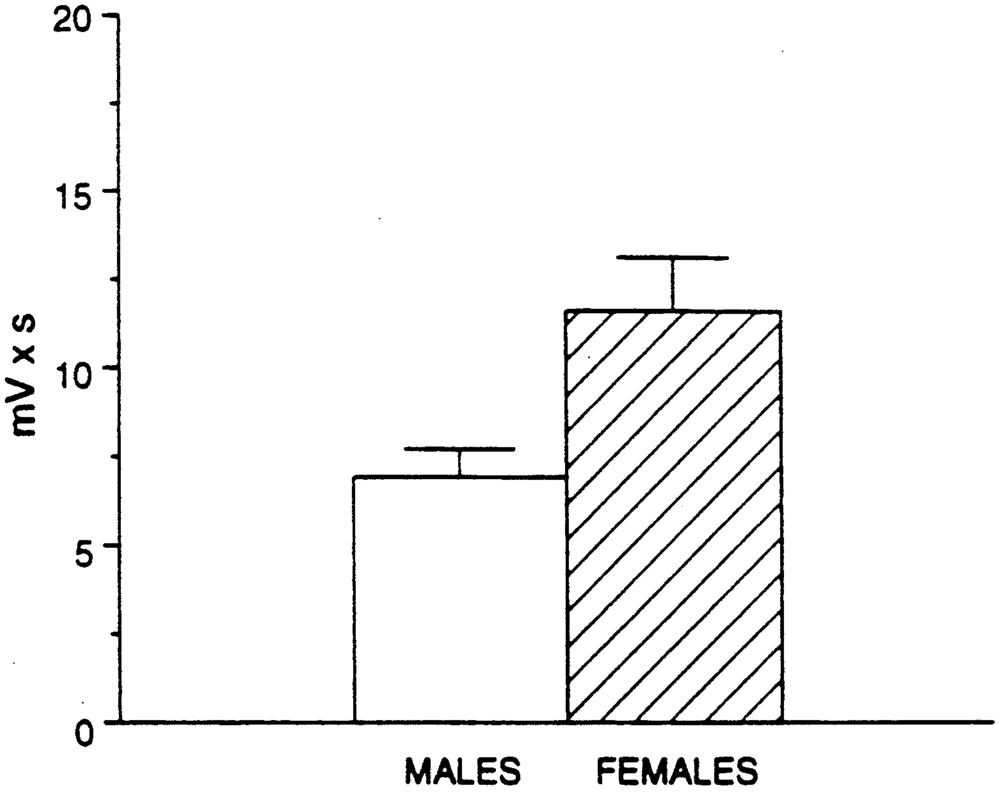
Figure 9C:
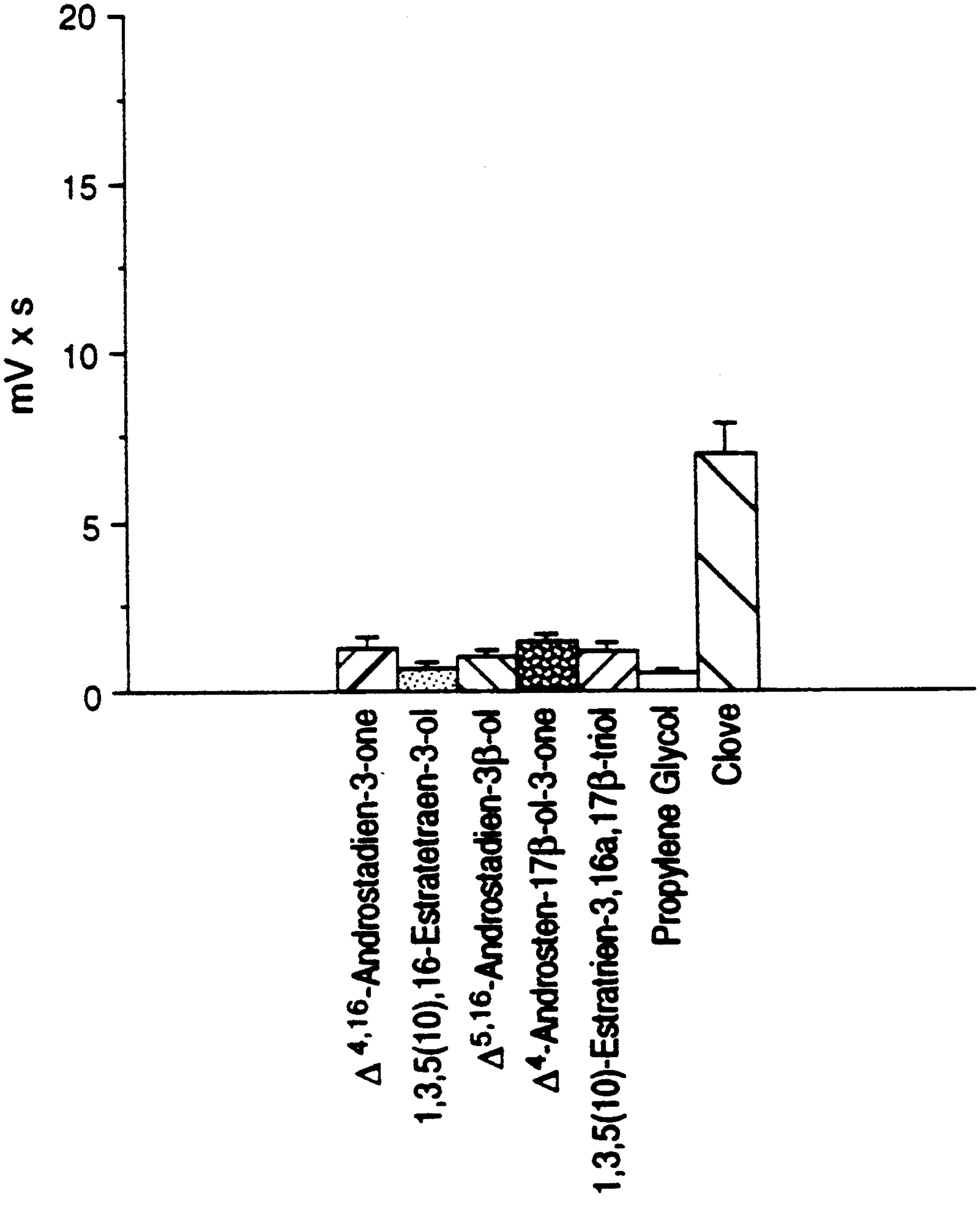
Figure 10A:
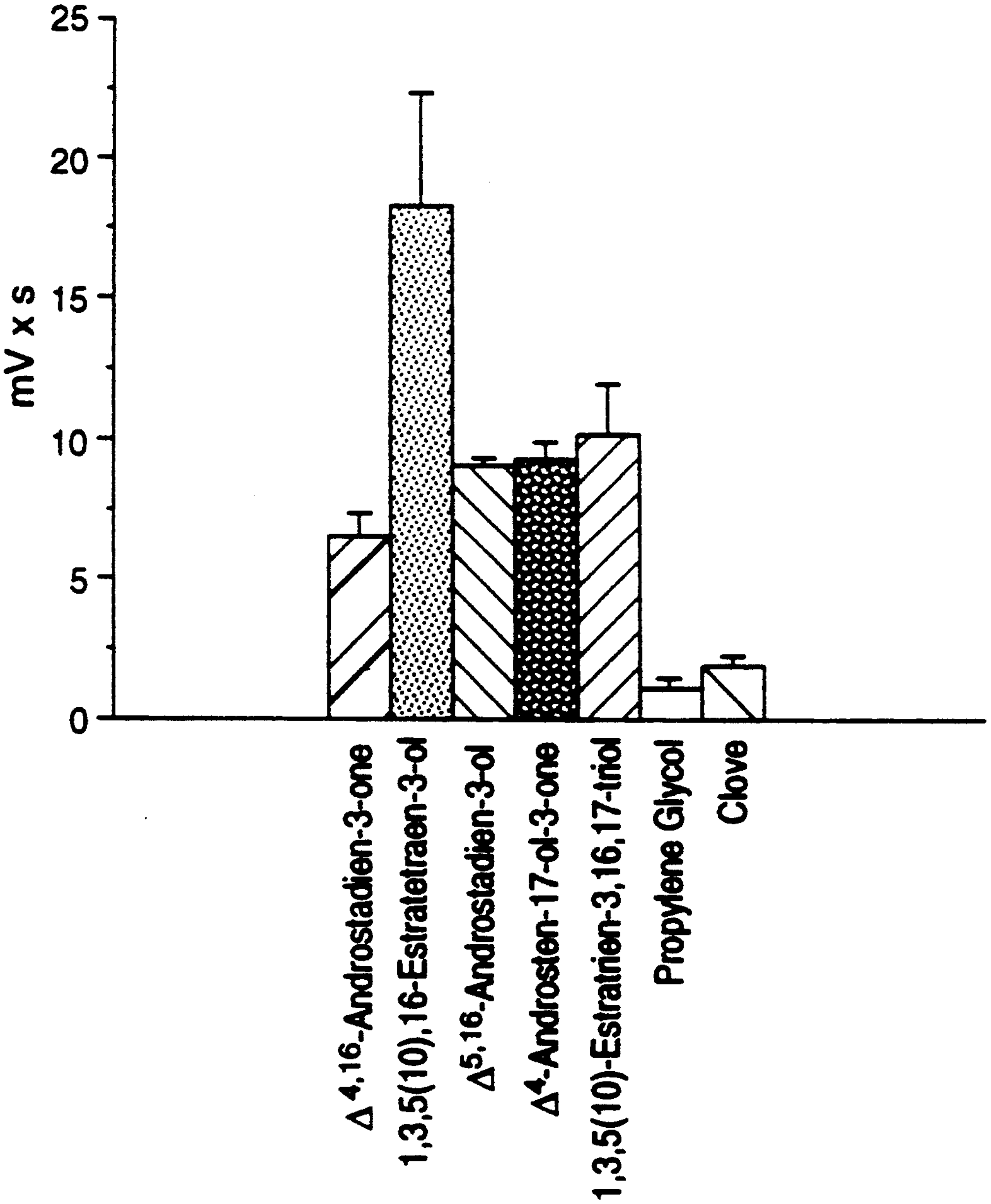
FIG. 10 is a graphic representation of the electrophysiological effect of the localized administration of particular Estrene steroids to the vomeronasal organ and to the olfactory epithelium.
Figure 10B:
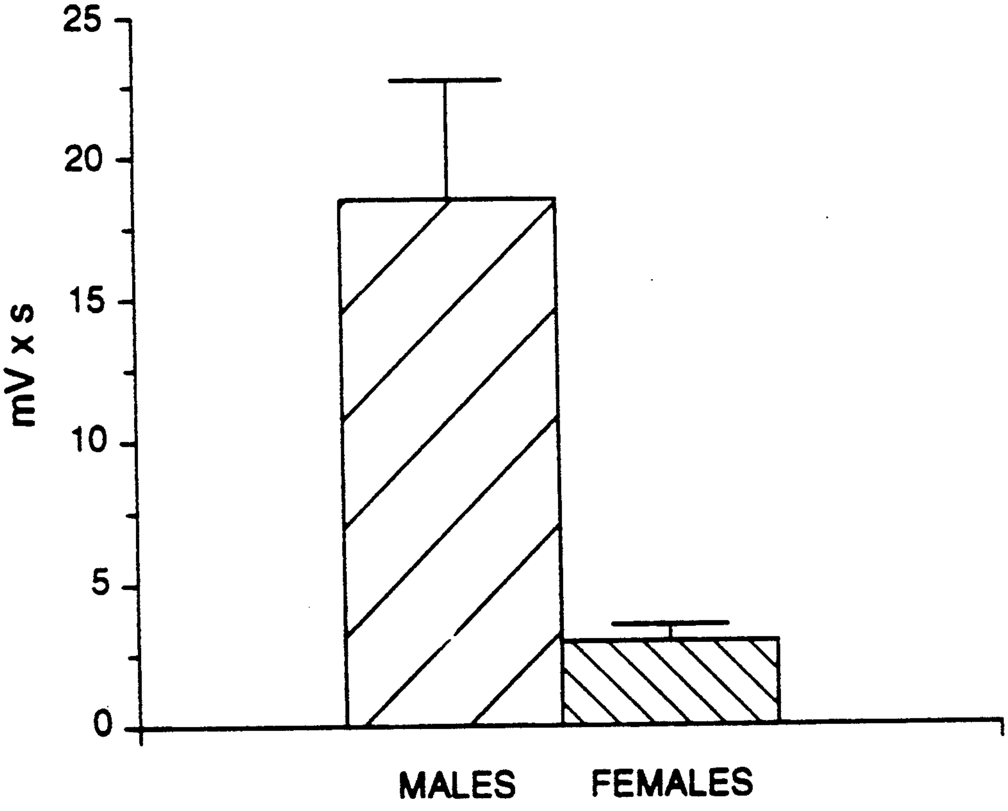
Figure 10C:
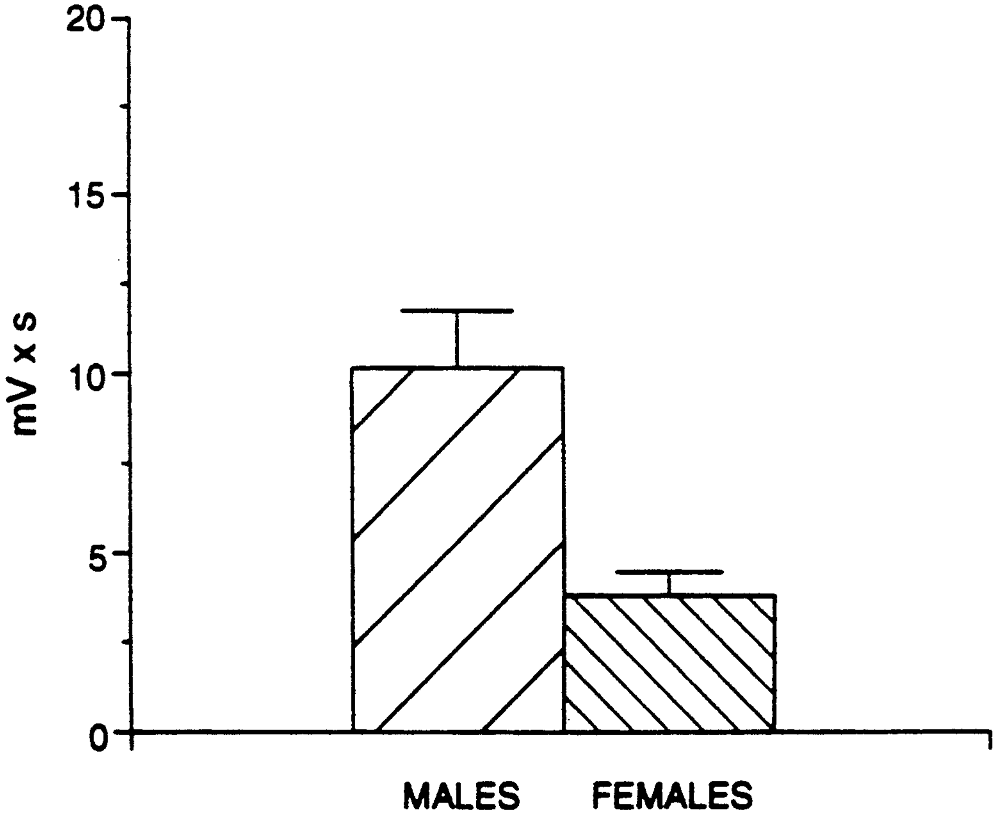
Figure 10D:
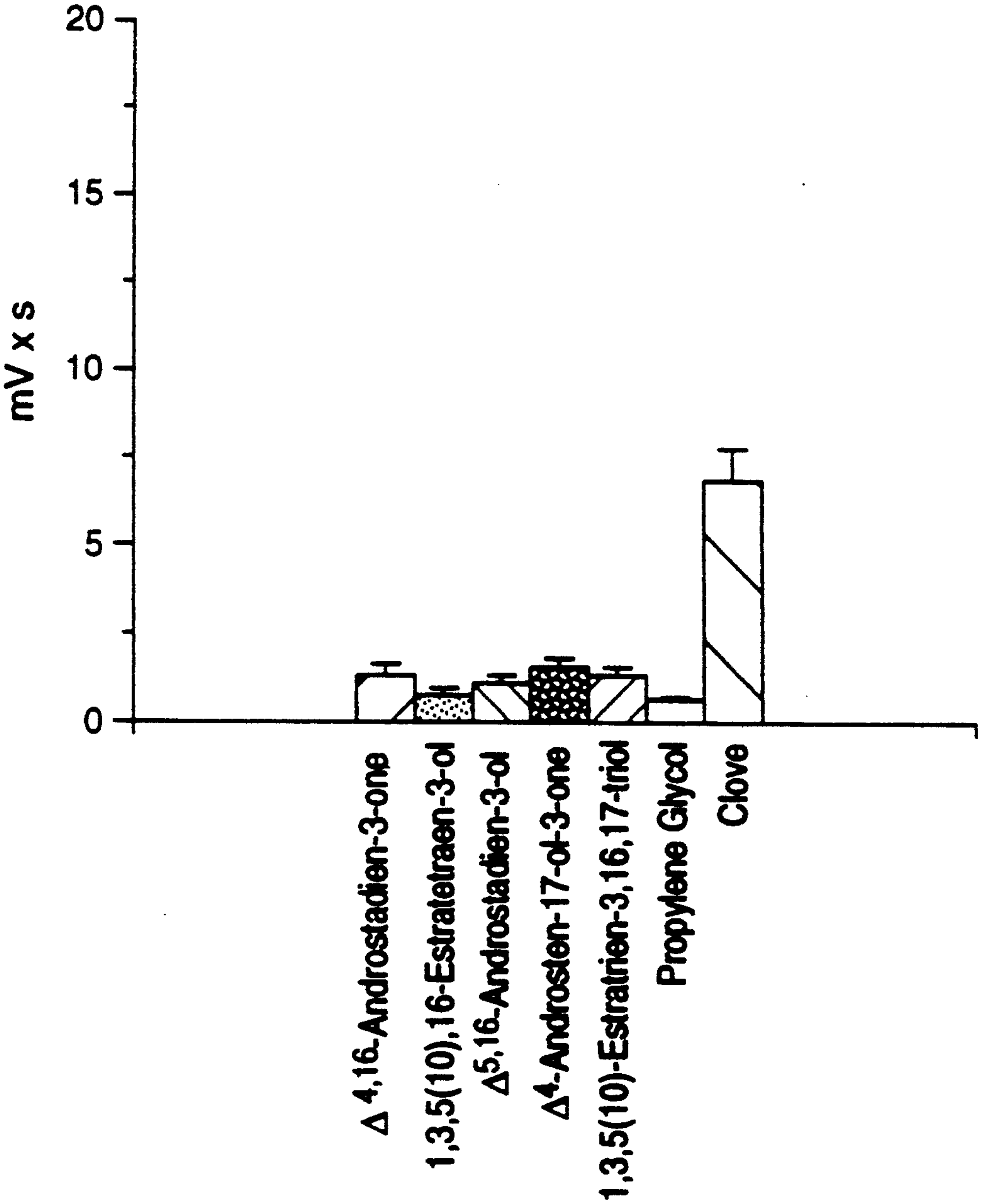

The results of this study are presented in FIG. 9. The response is a negative potential measured in millivolt-seconds (Mv x s). Δ4,16-androstadien-3-one elicits a significantly stronger VNO response in females than do the other compounds tested (FIG. 9A). Furthermore, the VNO response to Δ4,16-androstadien-3-one is sexually dimorphic—twice as strong in females as it is in males (FIG. 9B). In contrast, the OE response in both males and females is low compared to a strong odorant such as clove (FIG. 9C).

EXAMPLE 17

Electrophysiology of Estrene Stimulation of the Human VNO and Olfactory Epithelium A non-invasive method has been employed to record local electrical potentials from the human vomeronasal organ (VNO) and from the olfactory epithelium (OE). Localized gaseous stimulation was applied to both nasal structures at different instances using specially designed catheter/electrodes connected to a multichannel drug delivery system. The local response of the VNO and the OE showed a correlation with the concentration of the stimulus.

The study was performed on ten clinically normal (screened) volunteers—2 males and 8 females, ranging in age from 18 to 85 years. The studies were conducted without general or local anesthetics.

The catheter/electrodes were designed to deliver a localized stimulus and simultaneously record the response. In the case of VNO recording, the right nasal fosa of the subject was explored using a nasoscope (nasal specula) and the vomeronasal opening was localized close to the intersection of the anterior edge of the vomer and the nasal floor. The catheter/electrode was gently driven through the VNO-opening and the electrode tip placed in the organ's lumen at 1 to 3 mm from the opening. The nasoscope was then removed. In the case of the OE, recording the procedure was similar except the positioning of the catheter/electrode was gently placed deep in the lateral part of the medial nasal duct, reaching the olfactory mucosa.

Localized gaseous stimulation was done through the catheter/electrode. A constant stream of clean, nonodorous, humidified air at room temperature was continuously passed through a channel of the stimulating system. The stimulating substances were diluted in propylene glycol, mixed with the humidified air, and puffed for from 1 to 2 seconds through the catheter-/electrode. It is estimated that this administration provides about 25 ρg of steroid to the nasal cavity.

The results of this study are presented in FIG. 10. The response is a negative potential measured in millivolt-seconds (mV x s). 1,3,5(10),16-Estratetraen-3-ol elicits a significantly stronger VNO response in males than do the other compounds tested (FIG. 10A). 1,3,5(10)-Estratriene-3,16α,17β-triol also elicits a strong VNO response. Furthermore, the VNO response to these two estrenes is sexually dimorphic—approximately four times as strong in males as it is in females (FIG. 10B). In contrast, the OE response in both males and females is low compared to a strong odorant such as clove (FIG. 10C).

It will be apparent to those skilled in the art that the objects of this invention have been achieved by providing the compositions described herein. Various changes may be made in the structure of the pheromones and in the compositions containing pheromones without departing from the concept of the invention. Further, features of some compositions disclosed in this application may be employed with features of other compositions. Therefore, the scope of the invention is to be determined by the terminology of the following claims and the legal equivalents thereof.

I claim as my invention:

1. A non-therapeutic fragrance composition comprising an odorant and at least one human pheromone selected from the group of 16-Androstene steroids having the formula:

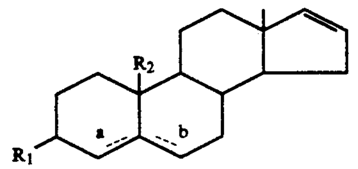

where $R_1$ is selected from the group consisting of oxo, α-(β-) hydroxy, α-(β-) acetoxy, α-(β-) propionoxy, α-(β-) methoxy, α-(β-) lower acyloxy, α-(β-) lower alkyloxy, and α-(β-) benzoyloxy; $R^2$ is selected from the group consisting of hydrogen, hydroxy, acyl, acyloxy, alkoxy, methyl, hydroxymethyl, acylmethyl, acyloxymethyl, alkoxymethyl, lower alkyl, hydroxyalkyl, acylalkyl, acyloxyalkyl, and alkoxylalkyl; and "a" and "b" are alternative sites for an optional double bond; and at least one Estrene steroid which has the formula:

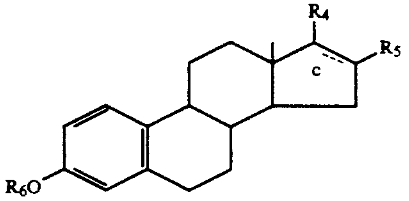

wherein $R_4$ is selected from the group consisting of hydrogen, alkyl, oxo, α-hydroxy, β-hydroxy, sulfate, cypionate, acetate, and glucuronide; $R_5$ is selected from the group consisting of hydrogen, α-hydroxy, and β-hydroxy; $R_6$ is selected from the group consisting of hydrogen, lower alkyl, benzoyl, cypionyl, acetyl, glucuronide, lower acyl and sulfate; and "c" is an optional double bond, said pheromone generating an in vivo vomeronasal organ negative receptor binding potential in a human subject.

2. The fragrance composition of claim 1 wherein said negative receptor binding potential is no less than about 5 vM X S.

3. The fragrance composition of claim 1 wherein said negative receptor binding potential is no less than about 10 mV X S.

4. The fragrance composition of claim 1 wherein said pheromone is selected from the group consisting of 4,16-Androstadien-3-one, 1,3,5(10),16-Estratetraen-3-ol and mixtures thereof.

5. The fragrance composition of claim 4 wherein the concentration of said pheromone in the fragrance composition is at least about 100 ng/ml, but no more than about 100 μg/ml.

6. The fragrance composition of claim 5 wherein the concentration of said pheromone in the fragrance is at least about 1 μg/ml, but no more than about 25 μg/ml.

7. The fragrance composition of claim 4 wherein said composition is formulated for external application to the skin.

8. The fragrance composition of claim 7 wherein the composition is a perfume.

9. A fragrance composition comprising at least one human pheromone selected from the group consisting of 16-Androstene steroids having the formula:

I

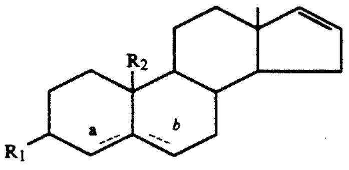

where $R_1$ is selected from the group consisting of oxo, α-(β-) hydroxy, α-(β-) acetoxy, α-(β-) propionoxy, α-(β-) methoxy, α-(β-) lower acyloxy, α-(β-) lower alkyloxy, and α-(β-) benzoyloxy; $R^2$ is selected from the group consisting of hydrogen, acylmethyl, acyloxymethyl, alkoxymethyl, lower alkyl, hydroxyalkyl, acylalkyl, acyloxyalkyl, and alkoxylalkyl; and "a" and "b" are alternative sites for a double bond.

10. The fragrance composition of claim 9 wherein the concentration of said pheromone in the fragrance composition is at least about 100 ng/ml, but no more than about 100 μg/ml.

11. The fragrance composition of claim 10 wherein the concentration of said pheromone in the fragrance composition is at least about 1 μg/ml, but no more than about 25 μg/ml.

12. The fragrance composition of claim 9 wherein said composition is formulated for external application to the skin.

13. The fragrance composition of claim 12 wherein the composition is a perfume.

14. A fragrance composition comprising at least one human pheromone selected from the group of Estrene steroids having the formula:

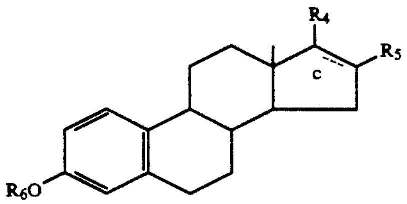

II wherein $R^4$ is selected from the group consisting of hydrogen, alkyl, oxo, α-hydroxy, β-hydroxy, sulfate, cypionate, acetate, and glucuronide; $R^5$ is selected from the group consisting of hydrogen, α-hydroxy, β-hydroxy; $R^6$ is selected from the group consisting of hydrogen, lower alkyl, benzoyl, cypionyl, acetyl, glucuronide, lower acyl and sulfate; and "a" is an optional double bond.

15. The fragrance composition of claim 14 wherein the concentration of said pheromone in the fragrance composition is at least about 100 ng/ml, but no more than about 100 μg/ml.

16. The fragrance composition of claim 15 wherein the concentration of said pheromone in the fragrance composition is at least about 1 μg/ml, but no more than about 25 μg/ml.

17. The fragrance composition of claim 14 wherein said composition is formulated for external application to the skin.

18. The fragrance composition of claim 17 wherein the composition is a perfume.

19. The fragrance composition of claim 1 wherein said 16-Androstene is $^{4,16}$Androstadien-3-one and said Estrene is 1,3,5(10),16-Estratetraen-3-ol.

20. The fragrance composition of claim 19 wherein the concentration of said pheromone in the fragrance composition is at least about 100 ng/ml, but no more than about 100 μg/ml.

21. The fragrance composition of claim 20 wherein the concentration of said pheromone in the fragrance composition is at least about 1 μg/ml, but no more than about 25 μg/ml.

22. The fragrance composition of claim 19 wherein said composition is formulated for external application to the skin.

23. The fragrance composition of claim 22 wherein the composition is a perfume.

24. A composition containing fibrous materials and at least one pheromone selected from the 16-Androstenes steroids specified in claim 9 or the Estrene steroids specified in claim 14.

25. The composition of claim 24 also containing an odorant.

26. A personal care product composition and at least one pheromone selected from the 16-Androstenes steroids specified in claim 9 or the Estrene steroids specified in claim 14.

* * * * *

UNITED STATES PATENT AND TRADEMARK OFFICE

CERTIFICATE OF CORRECTION

PATENT NO. : 5,272,134

DATED : December 21, 1993

INVENTOR(S) : David L. Berliner

It is certified that error appears in the above-identified patent and that said Letters Patent is hereby corrected as shown below:

Claim 14, column 22, lines 30-31, delete "and "a" is an optional double bond" and replace with --and "c" is an optional double bond--.

Signed and Sealed this

Nineteenth Day of May, 1998

Attest:

BRUCE LEHMAN

*Attesting Officer* *Commissioner of Patents and Trademarks*